US008070810B2

(12) United States Patent
Tarrant et al.

(10) Patent No.: US 8,070,810 B2
(45) Date of Patent: Dec. 6, 2011

(54) METHOD FOR REPAIR AND RECONSTRUCTION OF RUPTURED LIGAMENTS OR TENDONS AND FOR TREATMENT OF LIGAMENT AND TENDON INJURIES

(75) Inventors: Laurence J. B. Tarrant, Northampton, MA (US); Akihiko Kusanagi, Brookline, MA (US); Robert Lane Smith, Palo Alto, CA (US)

(73) Assignee: Histogenics Corporation, Waltham, MA (US)

( * ) Notice: Subject to any disclaimer, the term of this patent is extended or adjusted under 35 U.S.C. 154(b) by 577 days.

(21) Appl. No.: 11/653,024

(22) Filed: Jan. 12, 2007

(65) Prior Publication Data
US 2007/0162121 A1  Jul. 12, 2007

Related U.S. Application Data

(60) Provisional application No. 60/758,575, filed on Jan. 12, 2006.

(51) Int. Cl.
*A61F 2/08* (2006.01)
(52) U.S. Cl. .................... 623/13.12; 623/13.18; 623/908
(58) Field of Classification Search ..... 623/13.11–13.19
See application file for complete search history.

(56) References Cited

U.S. PATENT DOCUMENTS

| 5,614,587 | A  | * | 3/1997  | Rhee et al. ................... 525/54.1 |
| 6,443,988 | B2 | * | 9/2002  | Felt et al. ................... 623/17.12 |
| 6,533,821 | B1 |   | 3/2003  | Lally |
| 6,753,311 | B2 | * | 6/2004  | Fertala et al. ................ 514/17.2 |
| 7,524,513 | B2 | * | 4/2009  | Hai-Quan et al. ............ 424/443 |
| 2002/0062152 | A1 | * | 5/2002  | Dauner et al. ............. 623/13.18 |
| 2003/0225355 | A1 | * | 12/2003 | Butler ............................. 602/48 |
| 2004/0267362 | A1 |   | 12/2004 | Hwang et al. |
| 2005/0161857 | A1 | * | 7/2005  | Coombes et al. ........ 264/172.15 |
| 2005/0191248 | A1 | * | 9/2005  | Hunter et al. ................... 424/50 |
| 2008/0166329 | A1 | * | 7/2008  | Sung et al. ................... 424/93.7 |
| 2008/0287342 | A1 | * | 11/2008 | Yu et al. ........................... 514/2 |
| 2010/0291181 | A1 | * | 11/2010 | Uhrich et al. ................ 424/426 |

FOREIGN PATENT DOCUMENTS
EP       1 625 832 A1    2/2006  ............................ 2/2

OTHER PUBLICATIONS

Sardeli et al. "Use of porcine small intestinal submucosa in the surgical treatment of recurrent rectocele in a patient with Ehlers-Danlos syndrome type III." International Urogynecology Journal. vol. 16, pp. 504-505. 2005.*
Samuel Tozer, et al., Tendon and Ligament: Development, Repair and Disease,*Birth Defects Research*, (Part C) 75:226-236 (2005).
Bruce D. Beynnon, et al., Treatment of Anterior Cruciate Ligament Injuries, Part 1, *TheAmerican Journal of Sports Medicine*, 33/10:1579-1602, (2005).

(Continued)

*Primary Examiner* — Suzette J Gherbi
(74) *Attorney, Agent, or Firm* — Peters Verny, LLP

(57) ABSTRACT

A method and a means for repair and reconstruction of ruptured ligaments and tendons by in vivo or ex vivo repair and reconstruction surgical procedures. The method comprises providing a biodegradable sleeve placed around the frayed edges of an injured ligament or tendon for protecting the ligament or tendon injury with a protective shield. A composition comprising a biodegradable tissue adhesive applied on top of, around and/or between the frayed edges of the injured ligament.

16 Claims, 8 Drawing Sheets

OTHER PUBLICATIONS

Bruce D. Beynnon, et al., *Treatment of Anterior Cruciate Ligament Injuries, Part 2*, 33/11:1751-1767, (2005).

Terence Cruciate Woods, et al., Effectiveness of Three Extraction Techniques in the Development of a Decellularized Bone-Anterior Cruciate Ligament-Bone Graft, *Biomaterials*, 26:7339-7349, (2005).

M. J. Goertzen, et al., Anterior Cruciate Ligament Reconstruction Using Cryopreserved Irradiated Bone-ACL-Bone-Allograft Transplants, *Knee Surgery, Sports Traumatology, Arthroscopy*, 2/3: Abstract, (Sep. 1994).

Eiji Kondo, et al., Effects of Administration of Exogenous Growth Factors on Biomechanical Properties of the Elongation-Type Anterior Cruciate Ligament Injury With Partial Laceration, *TheAmerican Journal of Sports Medicine*, 33:188-196, (2005).

Nicholas G. Weiss, et al., Graft Selection in Surgical Reconstruction of the Multiple-Ligament-Injured Knee, *Operative Techniques in Sports Medicine*, 11/3:218-225, Abstract, (Jul. 2003).

F. Lincoln Avery, Anterior Cruciate Ligament (ACL) Graft Options, http://www.orthoassociates.com/ACL_grafts.htm, Internet Article, The Sports Medicine Center, 1-15.

* cited by examiner

RIGHT KNEE
MEDIAL VIEW

FEMUR

TIBIA          ACL

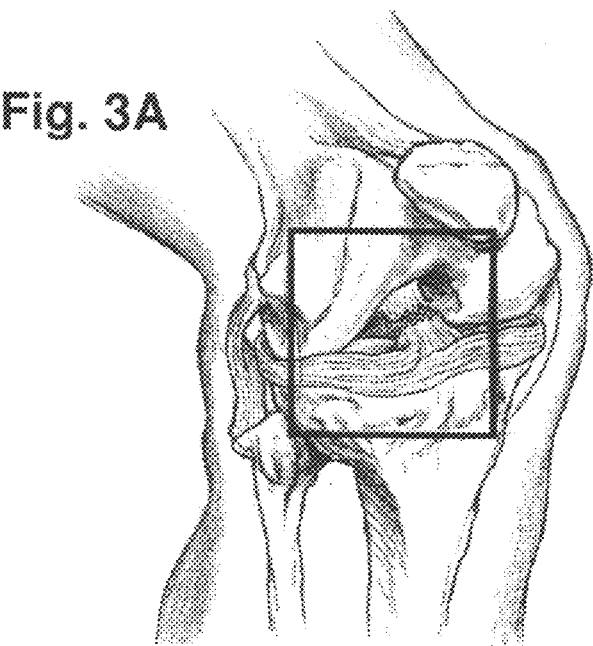
RIGHT KNEE
LATERAL VIEW
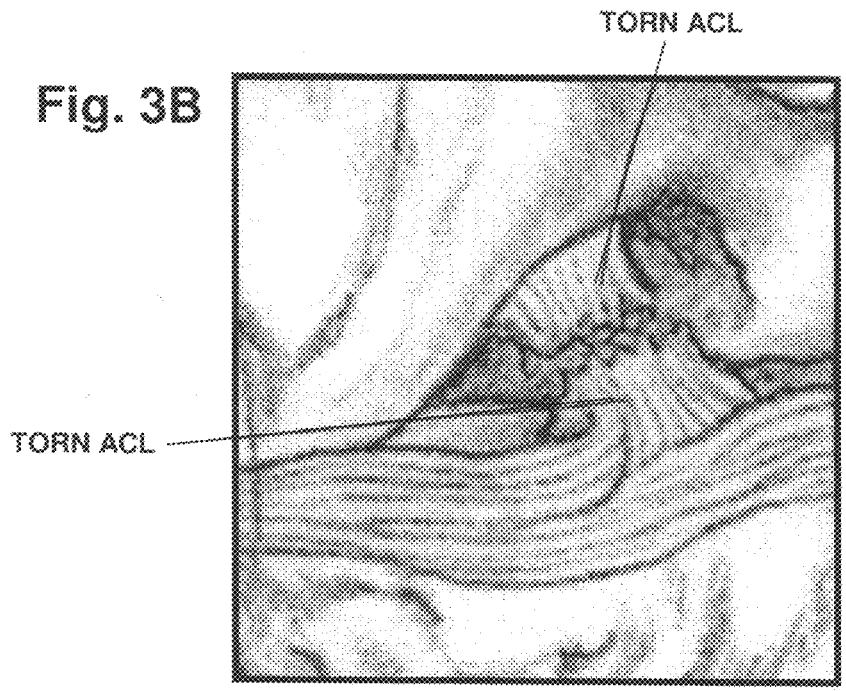

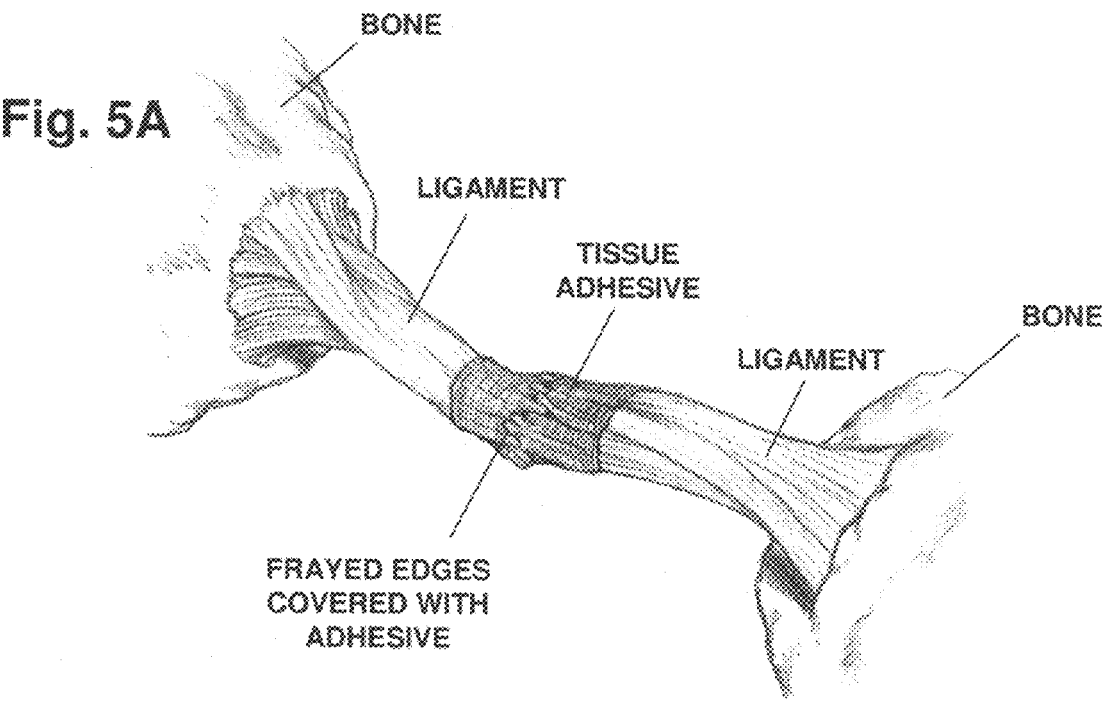
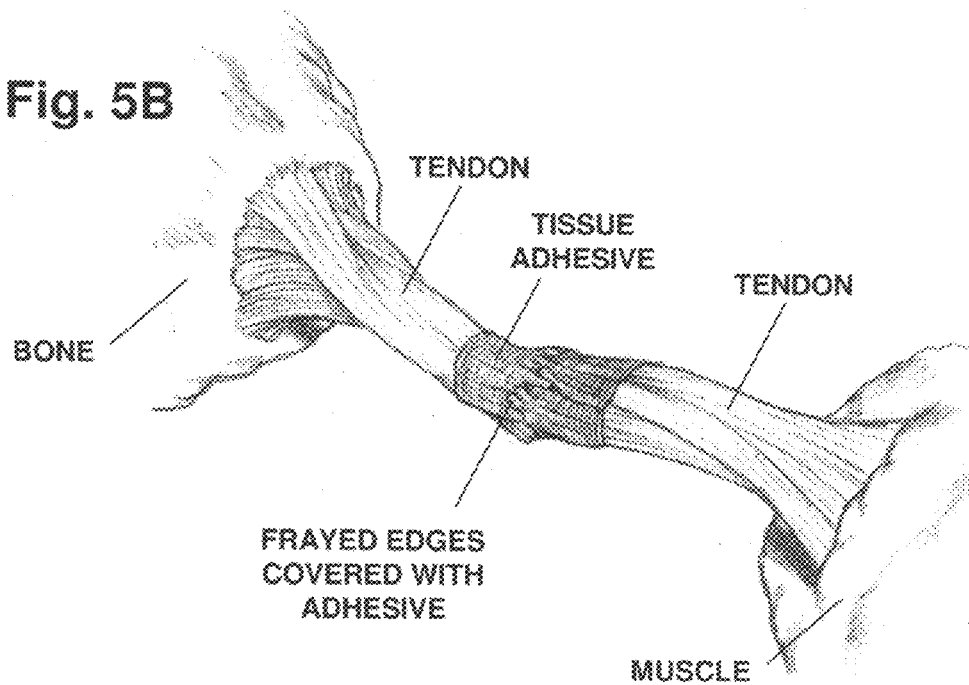

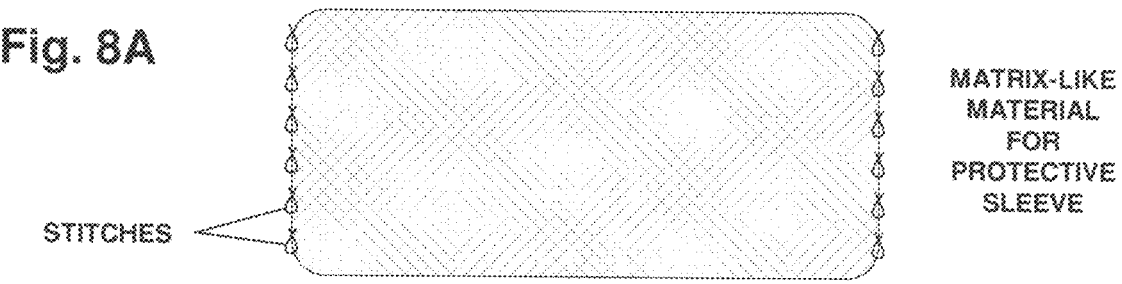
Fig. 8A — STITCHES; MATRIX-LIKE MATERIAL FOR PROTECTIVE SLEEVE
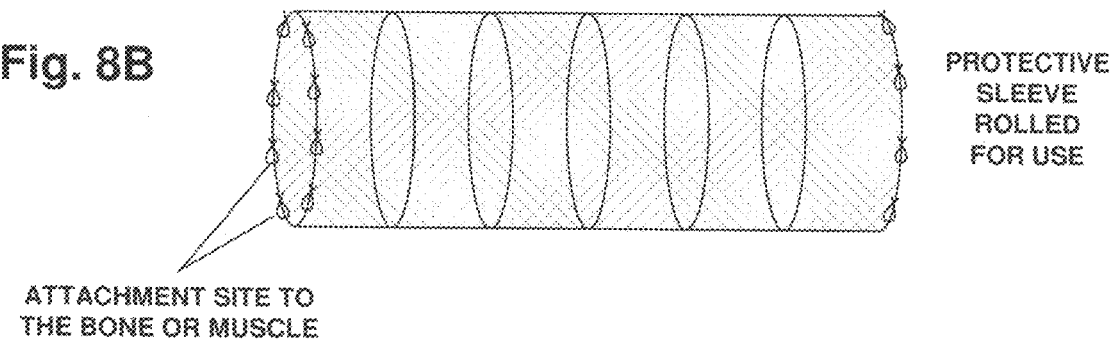
Fig. 8B — ATTACHMENT SITE TO THE BONE OR MUSCLE; PROTECTIVE SLEEVE ROLLED FOR USE
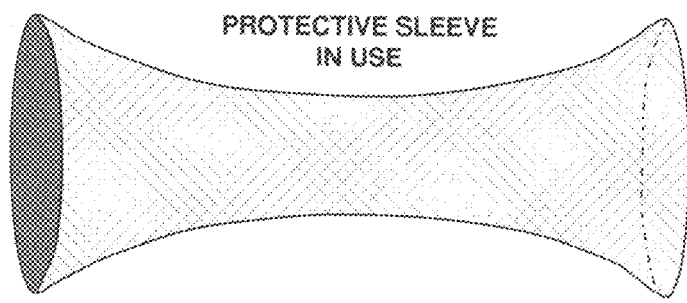
Fig. 8C — PROTECTIVE SLEEVE IN USE
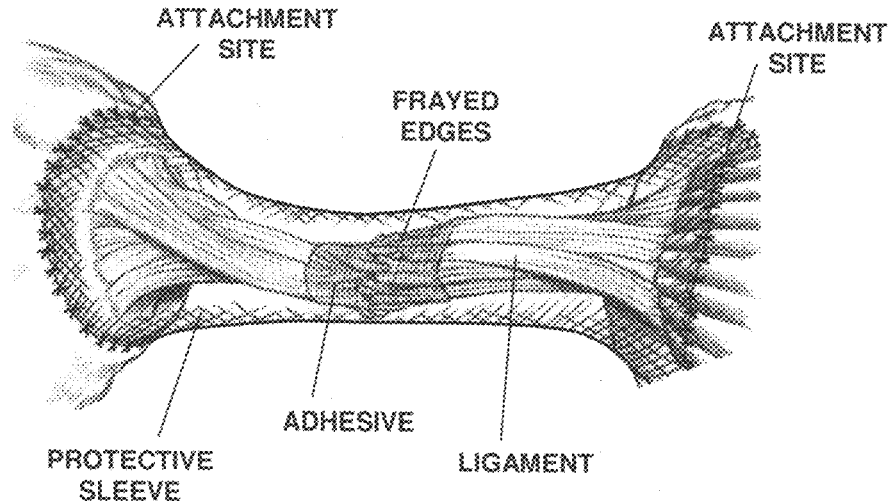
Fig. 8D — ATTACHMENT SITE; FRAYED EDGES; ATTACHMENT SITE; PROTECTIVE SLEEVE; ADHESIVE; LIGAMENT

METHOD FOR REPAIR AND RECONSTRUCTION OF RUPTURED LIGAMENTS OR TENDONS AND FOR TREATMENT OF LIGAMENT AND TENDON INJURIES

This application is based on and claims priority of the Provisional Application Ser. No. 60/758,575, filed on Jan. 12, 2006.

BACKGROUND OF THE INVENTION

Field of the Invention

This invention concerns a method and a means for repair and reconstruction of ruptured ligaments and tendons and for treatment of ligament and tendon injuries by in vivo and in situ performed procedures, or by ex vivo and in vitro culturing of the progenitor or mature fibroblast or tenocyte cells, stem or embryonic cells for augmenting the repair and reconstruction procedures or for production of the de novo ligament or tendon. The method is suitable for repair, reconstruction and regeneration of any ligament, tendon, intra-substance disruption or avulsion from the bone, particularly ligaments such as the hamstring or medial collateral and lateral collateral ligaments, or tendons such as the Achilles or rotator cuff tendons, and, in an appropriately modified form, the method is also suitable for repair and reconstruction of the anterior or posterior cruciate ligaments of the knee.

The method comprises a series of steps including attaching the edges of the ruptured ligament together, in situ, with a biodegradable tissue adhesive and providing a biodegradable sleeve for protecting the treated ligament or tendon rupture with a protective shield. The protective shield is placed around the frayed edges of a ruptured ligament or tendon before or after the frayed edges of the torn ligament or tendon are treated with a biologically acceptable and biodegradable tissue adhesive holding the separated edges of the ruptured ligament or tendon together for a period of time needed to heal the rupture.

The means for repair and reconstruction of ruptured ligaments and tendons include a composition comprising at least one biodegradable tissue adhesive suitable to be applied on top of, around and/or between the two edges of the ruptured ligament or tendon wherein said adhesive is typically a rapidly polymerizing compound having a sufficient strength to hold the frayed edges of the ruptured ligament or tendon together for a period of time needed for healing.

The device for repair and reconstruction of the ruptured ligaments or tendons comprises a biodegradable fibrous sheet, mesh, net or another matrix-like structure fabricated into a protective sleeve or sheath made of the biodegradable polymeric material having a predetermined degradation time for at least a time needed for the frayed edges of the ligament or tendon to grow together and, preferably, to heal. The protective sleeve has defined characteristics such as flexibility and contractibility that permits its shrinkage with extension of said sleeve. The polymeric material used for fabrication of the protective sleeve should be strong enough to withstand a tension largely corresponding to the tension to which the healthy functioning ligament or tendon is exposed during normal physical activity. The protective sleeve that functions as a protective shield for the treated ruptured ligament or tendon can be temporarily, until its biodegradation, attached to the uninjured portions of the torn ligaments or tendons on both sides, or to the bone or bones where the healthy ligament is normally attached or to the bone and muscle where the healthy tendon is attached as long as it provides a sufficiently strong support for the healing ruptured ligament or tendon. The flexible or contractible protective sleeve also functions to draw together or compress the ruptured tissue into a cohesive unit enabling close apposition of frayed ends or filamentous elements of the ligament or tendon leading to repair and reconstruction of the ligament or tendon.

BACKGROUND OF THE INVENTION

Injuries of the intra-articular and extra-articular tissues, including all ligaments and tendons injuries, such as injuries of the anterior cruciate collateral ligament (ACL), posterior cruciate ligament, rotator cuff tendon, Achilles tendon, meniscus and articular cartilage present numerous clinical problems. These tissues are unable to heal spontaneously and often fail to heal following the currently available treatments and surgical repair and reconstructions procedures.

Quite a few novel approaches, such as bioengineering of the new ligament or tendon, were recently described. For example, US application 2002/0062151 published on May 23, 2002 describes a method for producing an anterior cruciate ligament ex vivo; US application 2003/0100108 published on May 29, 2003 describes a matrix for production of tissue engineered ligaments for production of tissue engineered ligaments; US application 2003/0100108 published on May 29, 2003 describes a matrix for production of tissue engineered ligaments, tendons and other tissues ex vivo; U.S. Patent application 2004/0219659 published on Nov. 4, 2004 describes a bioreactor system for providing physiologically relevant translational and rotational strains of a growing bioengineered tissue, such as for example, ligament; U.S. Patent application 2004/0224406 published on Nov. 11, 2004 describes immunoneutral silk-fiber-based medical devices useful to form fabric for formation of tissue-supporting devices for implantation.

However, all these approaches are directed toward production of the new tissues ex vivo and it would thus be advantageous to have available methods for repair and reconstruction of ligaments and tendons in vivo and in situ settings.

Novel approaches to the repair and reconstruction of the articular cartilage have been previously described by inventors in, for example, U.S. Pat. No. 6,949,252, issued on Sep. 27, 2005, or the U.S. patent applications Ser. No. 10/625,245, filed on Jul. 22, 2003; Ser. No. 10/625,822, filed on Jul. 22, 2003; Ser. No. 10/882,581 filed on Jun. 30, 2004, allowed; Ser. No. 10/626,459, filed on Jul. 22, 2003; Ser. No. 10/921,389, filed on Aug. 18, 2004 and Ser. No. 10/998,230, filed on Nov. 24, 2004, issued as the U.S. Pat. No. 7,157,428 on Jan. 2, 2007, all hereby incorporated by reference.

The issued patents and applications disclose suitable adhesive sealants, materials suitable to be used as a support matrix, materials suitable for preparation of the supporting sleeves and methods for open, arthroscopic, or arthroscopic assisted surgical procedures similar to those involved in the current invention. All methods and materials disclosed in these patents and applications are hereby incorporated by reference to the extent that they are applicable to the current invention.

The current invention concerns a novel method for treatment and repair and reconstruction of the ligament and tendon injuries, tears or ruptures by utilizing biologically acceptable tissue adhesives that enable a fixation of the ruptured ligaments and tendons in a stable juxtaposition and promote their healing in situ as well as providing a means for protecting the treated site in situ for a period of time needed for healing. One advantage of this approach is that the ruptured or injured ligaments or tendons need not be partially or completely removed and replaced with the engineered ligaments or tendons, as described in the above-cited publications. Such replacement is an intricate process and an attachment of the replacement ligaments or tendons to the bones or muscles requires rather complicated surgical procedures.

The current invention provides conditions for treatment of the ligament or tendon injuries and tears in situ by permitting, during open, arthroscopic or arthroscopic assisted surgical procedures to find the loose frayed edges of the ruptured ligaments or tendons, and insofar as possible, fix these edges with a tissue adhesive in a stable juxtaposition similar to that found in the healthy tissue. Following the fixation with the tissue adhesive, the tear or rupture covered with and sealed with the adhesive is protected by the protective biodegradable sleeve optionally also containing a support matrix with or without exogenously added cells, such as, fibrocytes, tenocytes, progenitor, embryonic or stem cells, and additionally optionally supplemented with growth promoting factors, modulators or other agents added to the adhesive or embedded within the supporting matrix. The biodegradable time of the tissue adhesive and/or of the protective sleeve is designed to be at least as long as and/or to correspond to the time needed for healing.

All patents, patent applications and other publications disclosed herein are hereby incorporated by reference.

SUMMARY

One aspect of the current invention is a method for repair and reconstruction of ruptured ligaments or tendons.

Another aspect of the current invention is a method for repair and reconstruction of ruptured ligaments or tendons by providing a biodegradable sleeve for protecting the ligament or tendon rupture with a protective shield wherein the protective shield is placed around the frayed edges of a ruptured ligament or tendon or attached to an uninjured portion of the ligament or tendon or to the bone and/or muscle before or after the separated frayed edges of the ruptured ligament or tendon are juxtaposed as in the healthy tissue and treated with a biologically acceptable and biodegradable tissue adhesive holding the frayed edges of the ruptured ligament or tendon together for a period of time needed to heal the rupture, wherein the protective sleeve is placed along the portion of the partial or whole length of the ligament or tendon and is attached either to the uninjured portions of ligaments or tendons or to the bones or muscles situated on the opposite sides of the injured ligaments or tendons where the healthy ligament of tendon is normally attached.

Still another aspect of the current invention is a composition useful for repair and reconstruction of ruptured ligaments or tendons wherein said composition comprises at least one biodegradable tissue adhesive suitable to be applied on top of, around and/or between the two or more frayed edges of the ruptured ligaments or tendons and hold these edges together for a period of time needed for healing.

Yet another aspect of the current invention is a device for repair and reconstruction of ruptured ligaments or tendons and restoration of their functionality wherein said device for repair and reconstruction of the ruptured ligaments or tendons comprises a protective sleeve alone or a protective sleeve/ biodegradable support matrix composite made of the polymeric material that is strong enough to withstand a tension largely corresponding to the tension to which the healthy functioning ligament or tendon is exposed, and wherein said sleeve or composite has flexibility and contractibility that permits its contraction with extension, and that is suitable for temporary attachment to the uninjured portion of the ligament or tendon, or to the bone or muscle at a site where the healthy ligament is attached, or to the bone and muscle where the healthy tendon is attached.

Still yet another aspect of the current invention is a device for repair and reconstruction of ruptured ligaments or tendons and restoration of their full functionality wherein said device for repair and reconstruction of the ruptured ligaments or tendons comprises a protective sleeve alone or combined with a biodegradable support matrix as a composite made of the fiber material that is strong enough to withstand a tension largely corresponding to the tension to which the healthy functioning ligament or tendon is exposed, and that is suitable for temporary attachment to the uninjured portion of the ligament or tendon or to the bone where the healthy ligament is normally attached or to the muscle where the healthy tendon is normally attached, wherein said support matrix further optionally comprises cells, such as fibroblasts and/or tenocytes or their progenitors, stem or embryonic cells, and wherein said matrix may further optionally also include growth hormones, other modulators of tissue growth or suitable pharmaceutical agents.

Still yet another aspect of the current invention is a method for repair and reconstruction of ruptured ligaments or tendons and restoration of their function, said method comprising steps of:

(a) fabricating a protective sleeve that has flexibility and contractibility permitting its shrinkage with extension of said sleeve;

(b) selecting a biologically acceptable biodegradable tissue adhesive having a sufficiently fast setting time to set the tissue adhesive within about several minutes to have a sufficient strength to hold two or more frayed edges of ruptured ligaments or tendons together for at least a time needed for healing of said rupture or injury, that permits such ruptured ligaments or tendons to withstand the stress when subjected to stretching or other normal physiological activity during the healing period and biodegrade thereafter;

(c) surgically attaching one end of the protective sleeve to the uninjured portion of ligament or tendon, or to the bone where the unruptured healthy ligament or tendon is attached, wherein said protective sleeve may be attached alone or as a composite with a support matrix, wherein said support matrix may optionally contain exogenously added cells, growth factors, modulators or pharmaceutical agents;

(d) surgically stably juxtapositioning the two or more frayed edges of the ruptured ligament or tendon to a close proximity with each other wherein said proximity largely corresponds to the status quo of the uninjured healthy ligament or tendon;

(e) applying said tissue adhesive on the top, around and/or to said juxtaposed frayed edges of the torn ligament or tendon and thereby sealing a space between and around these frayed edges of the ruptured ligament or tendon with said tissue adhesive;

(f) pulling the protective sleeve over or otherwise covering the juxtaposed frayed edges of the ruptured ligaments or tendons sealed with the tissue adhesive with the protective sleeve;

(g) attaching a second end of the protective sleeve to the uninjured portion of the ligament or tendon or to the bone where the other end of the unruptured ligament is normally attached or to the muscle where the unruptured tendon is normally attached; and (h) stabilizing a site of the injury by limiting weight bearing and/or range or motion for a time needed for the frayed edges of the ruptured ligament or tendon to grow together and for the rupture to heal;

wherein said protective sleeve for repair and reconstruction of the ruptured ligaments or tendons comprises a biodegradable fibrous sheet, mesh, netting or a matrix-like material made of the biodegradable polymer, hydrogel, gel or thermoreversible hydrogel that is flexible, contractible and strong enough to withstand a tension largely corresponding to the tension to which the healthy functioning ligament or tendon is exposed and that is suitable for temporary attachment to the bone where the healthy ligament is attached or to the muscle where the healthy tendon is attached.

BRIEF DESCRIPTION OF DRAWINGS

FIG. 3A is a drawing of the right knee showing a ruptured ligament attached to the bones as viewed through arthroscopy. FIG. 3B is an enlarged inset section seen in FIG. 3A showing the torn anterior cruciate ligament attached to femur and tibia with two edges of the torn ligament clearly visible.

FIG. 5A is a schematic representation of a ruptured ligament seen in FIG. 4A treated with a tissue adhesive applied to the frayed juxtaposed edges of the tear and to the immediate vicinity of the tear. FIG. 5B is a schematic representation of a ruptured tendon treated with an adhesive applied to the frayed juxtaposed edges of to the tendon tear and to the immediate vicinity of the tear.

FIG. 8A is a schematic representation of a protective sheath before being used for encasement of a torn ligament or tendon. Exogenously added cells may be attached to the sheath before it is rolled into the protective sleeve, as seen in FIG. 8B. FIG. 8B shows the protective sheath rolled into the protective sleeve showing a site of a surgical attachment to the bone or muscle. FIG. 8C is a schematic representation of the protective sheath in use, wherein the middle portion of the sheath covering the area of treatment with a tissue adhesive is shown to be flexibly contracted. FIG. 8D shows the protective sleeve positioned around the ruptured frayed edges of the torn ligament or tendon treated with the tissue adhesive, compressing the frayed edges of the torn ligament or tendon.

DEFINITIONS

Figure 1:
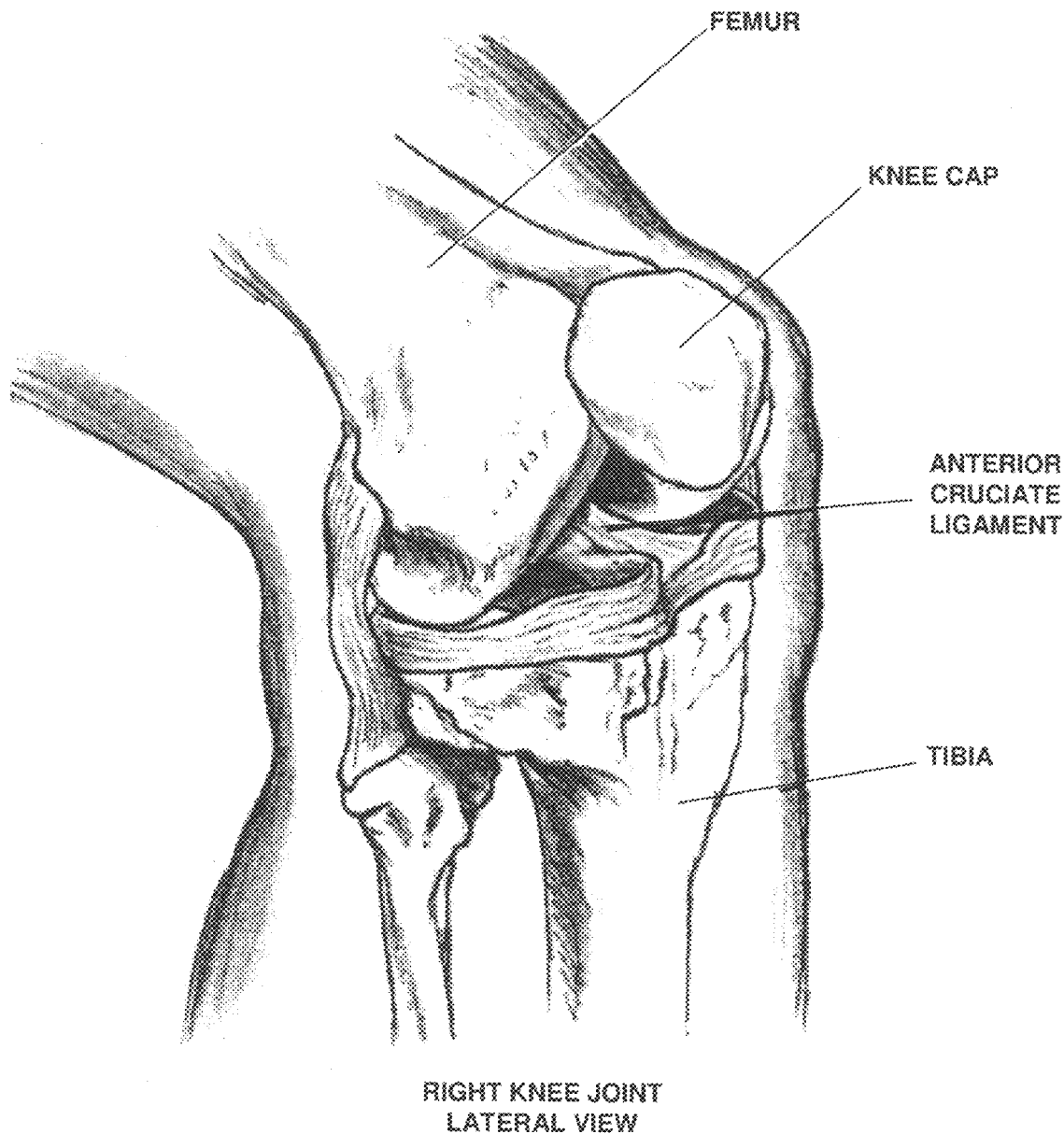
FIG. 1 is a lateral view of the right knee joint showing placement of the anterior cruciate ligament, knee cap, femur and tibia within the healthy knee.

As used herein:

"Repair", "reconstruction" or "regeneration" means any surgical procedure, such as open surgery, arthroscopic surgery or arthroscopically assisted surgery, suitable to be used in the practice of this invention that allows utilization of the juxtapositioning of the torn frayed edges of the ligaments or tendons, treatment of the torn area with a tissue adhesive and encasement of said area in the protective sheath that leads to the repair, reconstruction or regeneration of the ligament or tendon.

"Intra-substance disruption" means tearing apart of ligament or tendon wherein the tear or rupture is within anatomic structure of the ligament or tendon.

"Bone avulsion" or "avulsion fracture" means tearing and/or separation of the tissue where the tendon or ligament is injured in such a manner that it pulls off or contain a piece of bone.

"Flexibility" or "contractibility" means a characteristics of the material used for the fabrication of the protective sheath. The flexibility means that the material is flexible enough to permit an extension, widening, narrowing or other deformation of said sheath as well as, after having been flexibly extended, widened, narrowed or otherwise deformed, it has flexibility and ability to revert to its initial state, and wherein the contractible material permits its contraction to a shorter length or narrowing around the treated area and/or shrinkage with extension.

"Apposition of frayed ends" means bringing, during surgery, the two or more frayed edges of the torn ligament or tendon to a position that largely corresponds to the position the unruptured ligament or tendon would have.

"Encasement" means a process of enveloping a ruptured ligament treated with a tissue adhesive according to the invention with a protective sleeve that has an approximate length corresponding to the length of the normal healthy uninjured ligament or tendon. The encasement permits the ligament to heal within confines of the physiological tension parameters largely existing under normal conditions.

"Sleeve" or "sheath" means a protective shield acting as encasement for a ruptured ligament or tendon treated with a tissue adhesive under conditions promoting healing. The sleeve is made of a fibrous sheet, silk, mesh, net or a matrix-like material rolled around or otherwise positioned around the ruptured and treated ligament and attached to the uninjured ligament or tendon or to the bone on either side, or the rolled up tube of said material that is first pulled over the one edge of the torn ligament and attached to the bone on that side, then the two edges of the torn ligament are pulled together and the adhesive is applied into the tear and in the near vicinity to hold the two edges appositioned to be together. Before or after the tissue adhesive is fully set or applied, the sleeve is pulled over the treated ligament and attached to the uninjured portion of the ligament or tendon or to the bone or the muscle on the other side. When the protective sleeve is pulled over the frayed edges of the ligament or tendon before the tissue adhesive is applied or set, such adhesive may be added to the protective sleeve when already encasing and compressing the area of the injury.

"Protective shield" means a sleeve as defined above, held in place wherein said rolled and attached sleeve provides a protective shield against tensions to which the ligament or tendon is normally subjected during a normal physical activity which tension, if not controlled by the protective shield, would prevent healing of the ligament.

"Setting" or "setting time" means setting, solidifying or polymerization time to set the tissue adhesive within three minutes to give it a sufficient strength to hold two edges of a ruptured ligament or tendon together when such ligament or tendon is subjected to stretching. Setting time is between about 0.5 minutes minimum and about 10 minutes maximum, with preferred time between about 1 and 3 minutes.

"Support matrix" means biologically acceptable sol-gel or collagenous sponge, scaffold, honeycomb, hydrogel or a polymer of an aromatic organic acid that provides a structural support for the ligament or tendon during the healing period. The support matrix is prepared from such materials as Type I collagen, Type II collagen, Type IV collagen, gelatin, agarose, cell-contracted collagen containing proteoglycans, glycosaminoglycans or glycoproteins, polymers of aromatic organic acids, fibronectin, laminin, bioactive peptide growth factors, cytokines, elastin, fibrin, synthetic polymeric fibers made of poly-acids such as polylactic, polyglycolic or polyamino acids, polycaprolactones, polyamino acids, polypeptide gel, copolymers thereof and combinations thereof. The gel solution matrix may be a polymeric thermo-reversible gelling hydrogel. The support matrix is preferably biocompatible, biodegradable, hydrophilic, non-reactive, has a neutral charge and is able to have or has a defined structure.

"Adhesive", "tissue adhesive" or "glue" means a biologically acceptable typically rapidly gelling compound or formulation having a specified range of adhesive and cohesive properties, and is typically a hydrogel, such as derivatized polyethylene glycol (PEG), or a protein, such as albumin, which is preferably cross-linked with a collagen compound. The tissue adhesive of the invention typically gels and/or bonds rapidly upon contact with tissue, particularly with tissue containing collagen. A suitable adhesive for use in the invention has a polymerization time between about 30 seconds and about three minutes.

"Sol-gel" means a colloidal suspension which, under certain conditions, transitions from a liquid (sol) to a solid material (gel). The sol is a suspension of aqueous collagen that is transitioned, by heat treatment, into a gel.

"Thermo-reversible" means a compound or composition (not necessarily containing collagen) changing its physical properties such as viscosity and consistency, from sol to gel, depending on the temperature. The thermo-reversible composition is typically completely in a sol (liquid) state at between about 5 and 15° C. and in a gel (solid) state at about 25-30° C. and above. The gel/sol state in between shows a lesser or higher degree of viscosity and depends on the temperature. When the temperature is higher than 15° C., the sol begins to change into gel and with the temperature closer to 30-37° the sol becomes more and more solidified as gel. At lower temperatures, typically lower than 15° C., the sol has more liquid consistency.

"TRGH" means thermo-reversible gelation hydrogel material in which the sol-gel transition occurs on the opposite temperature cycle of agar and gelatin gels. Consequently, the viscous fluidic phase is in a sol stage and the solid phase is in a gel stage. TRGH has very quick sol-gel transformation which requires no cure time and occurs simply as a function of temperature without hysteresis. The sol-gel transition temperature can be set at any temperature in the range from 5° C. to 70° C. by molecular design of thermo-reversible gelation polymer (TGP), a high molecular weight polymer of which less than 5 wt % is enough for hydrogel formation.

"Connective tissue" means tissue that protects and supports the body organs, and also tissues that hold organs together. Examples of such tissues include mesenchyme, mucous, connective, reticular, elastic, collagenous, bone, blood, or cartilage tissue such as hyaline cartilage, fibrocartilage, and elastic cartilage.

"Adhesive strength" means a peel bond strength measurement, which can be accomplished by bonding two plastic tabs with an adhesive formulation and determining the strength of the bonding. A minimum force per width of 10 N/m is desired with 100 N/m or higher force preferred and more desirable.

"Cohesive strength" means the force required to achieve tensile failure and is measured using a tensile test apparatus. Force at extensional failure should be at least 0.2 MPa (2 $N/cm^2$) but preferably 0.8 to 1 MPa or higher.

"Lap shear measurements" means a test of bonding strength, in which the adhesive formulation is applied to overlapping tabs of tissue, cured, and then the force to pull the tabs apart is measured. The test reflects adhesive and cohesive bonding; strong adhesives have values of from 0.5 up to 4-6 $N/cm^2$ of overlap area.

DETAILED DESCRIPTION OF THE INVENTION

This invention concerns a method, device and a means for repair and reconstruction of ruptured ligaments and tendons and for treatment of ligament and tendon injuries by preferably in vivo and in situ performed repair and reconstruction using open, arthroscopic or arthroscopically assisted surgical procedures, as described herein below. Ex vivo repair and reconstruction procedures could similarly be performed using techniques and procedures described herein.

The method is particularly suitable for repair and reconstruction and regeneration of practically all ligaments and tendons, represented by hamstring or medial collateral and lateral collateral ligaments or Achilles or rotator cuff tendons and, in a modified form, is also useful for repair and reconstruction of anterior or posterior cruciate ligaments of the knee.

The method comprises providing a biodegradable sleeve for protecting the ligament or tendon rupture with a protective shield for the time needed for healing. The protective shield is placed around the frayed edges of the ruptured ligament or tendon before or after the frayed edges are treated with a biologically acceptable and biodegradable tissue adhesive holding the frayed edges in stable juxtaposition for a period of time needed to heal the injury.

The means for repair and reconstruction of ruptured ligaments and tendons includes a composition comprising at least one biodegradable tissue adhesive suitable to be applied on top of, around and/or between the frayed edges of the ruptured ligament and hold these edges together for a period of time needed for healing.

The device for repair and reconstruction of the ruptured ligaments or tendons comprises a biodegradable fibrous sheet, mesh, net or another matrix-like structure fabricated into a protective sleeve or sheath that may be used alone or is, preferably, used as a composite of the protective sleeve and a support matrix made of the biodegradable polymeric material having a predetermined degradation time corresponding to at least a time needed for frayed edges of the ligament or tendon to grow together and, preferably, to heal. The protective sleeve or the composite has defined characteristics such as flexibility and contractibility that permits its contraction with extension of said sleeve thereby compressing the area of the frayed edges treated with the tissue adhesive. The polymeric material used for fabrication of the protective sleeve should be strong enough to withstand a tension largely corresponding to the tension to which the healthy functioning ligament or tendon is exposed during normal physical activity.

The protective sleeve that functions as a protective shield for the treated ruptured ligament or tendon can be temporarily, until its biodegradation, attached to the uninjured portion of the ligament or tendon or to the torn ligament or tendon on both sides, or to the bone or bones where the healthy ligament is normally attached or to the bone and muscle where the healthy tendon is attached as long as it provides a sufficiently strong shield for the ruptured ligament or tendon. The flexible or contractible protective sleeve or the composite is also able to draw together or compress the ruptured tissue into a cohesive unit enabling close apposition of frayed ends or filamentous elements of the ligament or tendon leading to repair and reconstruction of the ligament or tendon.

The repair and reconstruction procedures described herein may be advantageously supplemented by exogenously added cells, such as fibroblasts, tenocytes, their progenitors, stem or embryonic cells. These cells are typically commercially available or are isolated and cultured in vitro before being added to the support matrix. The progenitor or mature fibroblasts or tenocytes, embryonic or stem cells are added to, or to the vicinity of, the tissue adhesive, or are incorporated, adhered to, embedded or seeded into the supporting matrix of the protective sleeve composite. The added cells promote healing, speed up the transport and movement of endogenous cells from the uninjured portions of ligaments or tendons into the healing site, and/or support production of the de novo ligament or tendon within the confines of the protective sleeve or matrix.

I. Ligaments and Tendons

Ligaments are strong dense structures made of connective tissue that fasten bone to bone and stabilize a joint. There are numerous ligaments in the body. While this invention is preferably useful for treatment of all ruptured ligaments and tendons, such as, for example, medial collateral and lateral collateral ligaments, hamstring ligament, Achilles or rotator cuff tendons, the method may, in a modified form be also useful for treatment of the anterior or posterior cruciate ligaments.

Ligament is a band or sheet of fibrous tissue connecting two or more bones, cartilages or other structures or serving as a support for fasciae or muscles.

Tendon is a fibrous cord or band of variable length that connects a muscle with the bone or with other structures. Tendon consist of fascicles of very densely arranged, almost parallel collagenous fibers containing rows of elongated fibrocytes. In many ways the tendons function in the same way as ligaments, however, they typically connect bone to muscle or muscle to muscle.

Some of the ligaments have a very intricate anatomical architecture and orientation and their injuries are, therefore, very difficult to treat. A good example of such ligament is the anterior cruciate ligament (ACL). The anatomical characteristics of healthy joints and sites of the of the ACL injuries are provided in FIGS. 1-3 for illustrative purposes.

Anterior cruciate ligament is ligament that extends from the anterior intercondylar (between two condyles) area of the tibia to the posterior part of the medial surface of the lateral condyle, a rounded articular surface at the extremity of the femur.

The function of the anterior or posterior cruciate ligaments of the knee as well as medial collateral and lateral collateral ligaments is to provide stability to the knee and minimize stress across the knee joint, to restrain excessive forward movement of the lower leg bone (tibia) in relation to the thigh bone (the femur) and to limit rotational movements of the knee. When any one of those ligaments is injured or ruptured, the control of the knee movements is disturbed. Due to a bone to bone attachment of the ligaments to the femur and tibia, two torn and separated edges of the ligament are constantly pulled away from each other.

Anatomical illustration of the knee and the anterior cruciate ligament vis-a-vis the femur and tibia is seen in FIG. 1. FIG. 1 shows relative positions of the femur, tibia and knee cap as well as anterior cruciate ligament and the collateral ligament. As seen in FIG. 1, the anterior and posterior cruciate ligaments cross the center of the knee. The lateral and medial collateral ligaments are located outside of the knee joint, on the outer and inner side of the knee. They act to stabilize the sideway motion of the knee. Since these ligaments literally hold the knee together and enable it to function in a way it is supposed to function, it is understandable that they are often subject to injuries and that the treatment of these injuries is difficult as these ligaments are constantly subjected to the tensile and rotating strain during any motion of the knee. Natural healing of the ligaments is essentially non-existent. Surgical sewing of the two edges of the ruptured ligament does not work because the site is constantly subjected to the above mentioned tensile and rotation strains and pulls.

Figure 2A:
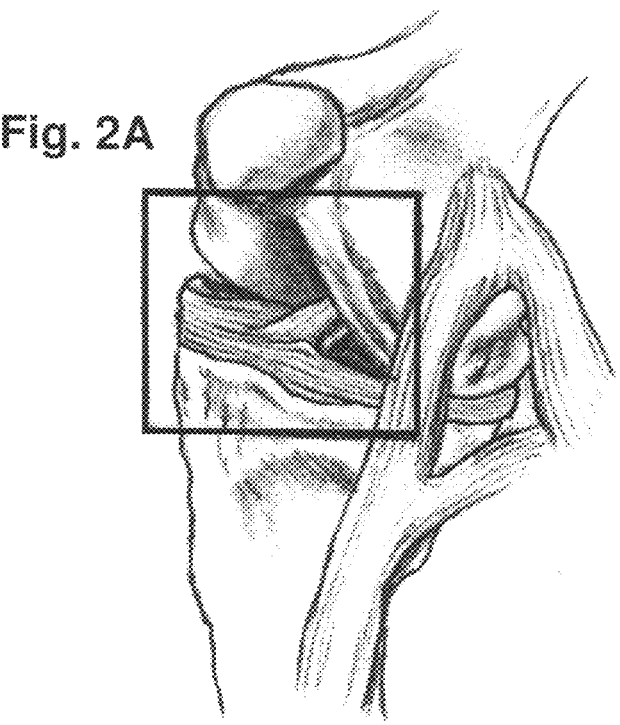
FIG. 2A is a drawing of the right knee showing a healthy ligament attached to the bones.
Figure 2B:
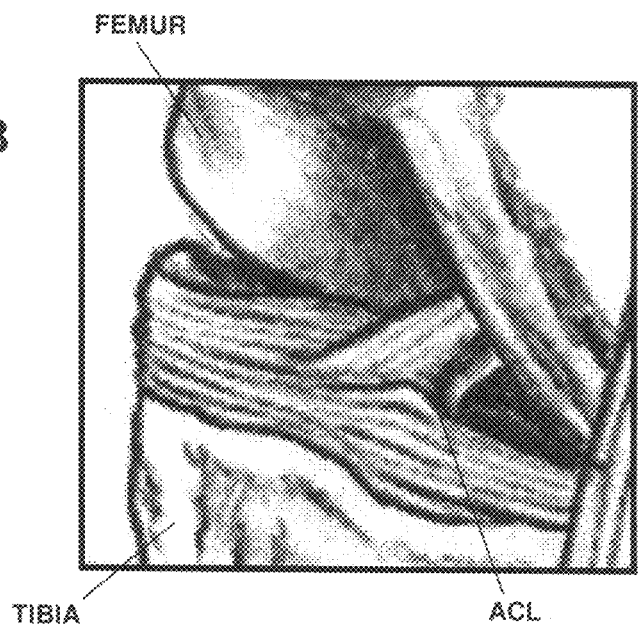
FIG. 2B is an enlarged inset section seen in FIG. 2A showing the anterior cruciate ligament attached to femur and tibia.

FIG. 2A is a medial view of the right knee showing a healthy ligament attached to the femur and tibia bones. FIG. 2B is an enlarged inset section seen in FIG. 2A showing the anterior cruciate ligament attached to femur and tibia. As seen in FIG. 2B, the ligament is a cord-like band or sheet of fibrous tissue that is typically attached on both ends to bones adjacent to articular surface, in this case tibia and femur.

FIG. 3A is a lateral view of the right knee showing a ruptured ligament attached to the femur and tibia bones as viewed through arthroscopy. FIG. 3B is an enlarged inset section seen in FIG. 3A showing the torn anterior cruciate ligament attached to femur and tibia with the two edges of the torn ligament clearly visible. Although the ligament is torn into two pieces with frayed edges, each piece remains firmly attached to either the femur or to the tibia. Since the tensile strain is strong, the two pieces of the torn ligament cannot be brought together solely by sewing them surgically because no surgical stitches could withstand the strain.

The current invention provides a practical method for repair and reconstruction of ligament and tendon injuries.

A method for repair and reconstruction of ligaments and tendons according to this invention comprises of the same steps, procedures and utilizes the same materials and devices.

II. Device for Repair and Reconstruction of Ligaments and Tendons

The device for repair and reconstruction of the ruptured ligaments or tendons comprises a protective sleeve alone or a composite of the protective sleeve and support matrix serving as a support structure for a torn ligament or tendon treated according to the invention. The support matrix may be supplemented with exogenously added cells, such as fibrocytes, tenocytes, their progenitors, mesenchymal, stem or embryonic cell.

The protective sleeve or the composite is fabricated from biodegradable polymeric materials that are strong enough to withstand tension corresponding largely to the tension to which the healthy functioning ligament or tendon is exposed. The material must be suitable for temporary attachment to the ligament or tendon or to the bone or muscle where the healthy ligament or healthy tendon is normally attached.

For the purposes of this invention and in order to treat the ligament or tendon injury or tear, the protective sleeve or the composite is attached either to the uninjured portion of the ligament or to the uninjured portion of the tendon, on one or both sides of the tear, or it is attached to the bones on both sides, in case of the ligament, or to the bone on one side and muscle on the other side, in case of the tendon, or it may be also attached to the uninjured portion of the ligament or tendon and to the bone or muscle on the other side, depending on the injury or tear.

1. Protective Sleeve and the Protective Sleeve/Support Matrix Composite

The protective sleeve or a composite of the protective sleeve with a support matrix for use in this invention is made of a strong, flexible and contractible material. The material is biologically acceptable and biodegradable. One primary requirement is that it is strong enough to withstand the tensile or rotation forces of the bones and that such strength at least largely equals to or is higher than the forces asserted in the healthy uninjured ligament by bones. Additionally, the biodegradable material must have predetermined time of degradation so that it does not degrade before the tear or rupture of the ligament or tendon is healed.

Typically, the material used for fabrication of the protective sleeve or the composite is a fibrous sheet, mesh, net or a matrix-like material and may be a mesh, fibers, knitted strands, knitted fibers, silk, silk fibers, polymer or a derivatized polymer.

Typically, the sleeve material is fabricated or supplied in a form of a sheet having a rectangular shape, a flat sheath, flat sheet formed into tubing or a flat mesh or a mesh tubing.

The protective sleeve or the composite is prepackaged for a surgeons use in variable sizes, lengths, and shapes. The prepackage form is provided in the sterile conditions for immediate use during surgery.

One embodiment of the protective sleeve comprises a knitted sheath from individual strands of yarn or any other suitable material wherein each strand of yarn comprises several fibers, for example, three fibers. Each fiber within the strand has a different function and degradation time. This time-different degradation allows for gradual degradation of the protective sleeve where the reconstructed, repairing or regenerating ligament or tendon is gradually subjected to certain decreasing tensile strength until the sufficiently healed ligament or tendon is able to assume its normal function.

In this embodiment, the first fiber to degrade has the primary purpose of supporting the deposition and growth of the incipient ligament-producing fibroblasts adjacent to the reconstructed or regenerating ligament. The first fiber may carry a negative surface charge in order to promote fibroblast attachment. The degradation time for the first fiber is about or less than one month. The first fiber is, for example, a derivatized block polyethylene glycol (PEG), a block PEG copolymer derivatized with a poly acid, for example, the block PEG-fumarate. Exemplary compounds suitable to be used for this purposes are those disclosed in the U.S. Pat. No. 5,527,864, issued on Jun. 18, 1996, herein incorporated by reference.

The second fiber to degrade reinforces the initial strength of the supporting sleeve. Its degradation time is about one to two months. This intermediate fiber is, for example, the Tepha microbially synthesized polyester polyalkanoates, or the TyRx poly-acrylate. However, it may also be the same fiber as used for the first fiber having, however, different degradation properties. These types of fibers are strong and tough but biodegradable.

The third fiber to degrade is the strongest one and provides the long-term backbone support for the protective sleeve and its degradation time is from about three to about six months. This long term support fiber is, for example, a mixture of the fibers described above.

In another embodiment, the protective sleeve is made of the silk fibers. Such silk fibers have been described in the U.S. patent applications 2004/0224406 published on Nov. 11, 2004 or 2003/0100108 published on May 29, 2003.

The other material, such as those described below for fabrication of the support matrix may also be advantageously used for preparation of the protective sleeve.

The device of the invention may be the protective sleeve alone but it preferably comprises a support matrix, typically fabricated from the same or a different material. Two components may be fabricated and used during the surgery together or separately.

2. Support Matrix

The support matrix may be stand alone structure or be a part of the protective sleeve/support matrix composite and typically provides a supporting structure strengthening the protective sleeve and may also provide a support for exogenously added cells, as described herein.

The support matrix is typically porous, sponge, honeycomb, lattice or scaffold structure made of collagenous or collagen containing material. The support matrix is preferably biocompatible, biodegradable, hydrophilic, non-reactive, has a neutral charge and is able to have or has a defined structure. The support matrix is fabricated from materials such as Type I collagen, Type II collagen, Type IV collagen, gelatin, agarose, or derivatized or cross-linked collagen, collagen containing proteoglycans, glycosaminoglycans or glycoproteins, polymers of aromatic organic acids, fibronectin, laminin, bioactive peptide growth factors, cytokines, elastin, fibrin, synthetic polymeric fiber made of poly-acids such as polylactic, polyglycolic or polyamino acids, polycaprolactones, polyamino acids, polypeptide gel, copolymers thereof, mixtures thereof and any and all combinations thereof.

All the above listed materials, or similar materials having required properties, or their combinations may be advantageously used alone or in combination as long as the produced mesh or fibers have enough strength to provide a support for the protective sleeve or in alternative may be used as a support matrix deposited between the tissue adhesive and said protective sleeve for further strengthening of its protective function.

Alternative material that may be advantageously used as a support matrix for the protective sleeve are sols, gels and thermoreversible hydrogels.

Thermoreversible gelling hydrogels are compounds or compositions changing its physical properties such as viscosity and consistency, from sol to gel, depending on the temperature. The thermo-reversible composition is typically completely in a sol (liquid) state at between about 5 and 15° C. and in a gel (solid) state at about 25-30° C. and above. The gel/sol state in between shows a lesser or higher degree of viscosity and depends on the temperature. When the temperature is higher than 15° C., the sol begins to change into gel and with the temperature closer to 30-37° the sol becomes more and more solidified as gel. At lower temperatures, typically lower than 15° C., the sol has more liquid consistency. Sol-gel transition of the thermo-reversible gelation hydrogel material occurs on the opposite temperature cycle of agar and gelatin gels. Consequently, the viscous fluidic phase is in a sol stage and the solid phase is in a gel stage. TRGH has very quick sol-gel transformation which requires no cure time and occurs simply as a function of temperature without hysteresis. The sol-gel transition temperature can be set at any temperature in the range from 5° C. to 70° C. by molecular design of thermo-reversible gelation polymer (TGP), a high molecular weight polymer of which less than 5 wt % is enough for hydrogel formation. Sol-gel or TRGH may be conveniently used as a supporting matrix as it can be deposited as a cooled sol, that is in a liquid state, during surgery and it will change to the gel state upon warming to the body temperature.

Additionally, the matrix may be a simple sol-gel solution, a colloidal suspension which, under certain conditions, transitions from a liquid (sol) to a solid material (gel). The sol is a suspension of aqueous collagen that is transitioned, by heat treatment, into a gel.

The support matrix is typically used as a support structure for exogenously adding, adhering, incorporating, embedding or seeding cells, such as fibroblasts, tenocytes, their progenitors, mesenchymal cells, stem or embryonic cells to the site of treatment. These cells are added in order to attenuate the treatment according to the invention or to increase or provide stimulation for the migration of the cells from the uninjured tissue. Suitable cells to be used in this invention are the cells that are either autologous or heterologous cells, such as allogenic or xenogenic cells, cell lines and/or procaryotic cells.

Typically, the cells added exogenously to the support matrix or to a collagenous scaffold are obtained commercially or isolated from the ligaments or tendons and cultured in vitro using methods know in the art.

The method, in one embodiment, comprises the in vitro and ex vivo addition of progenitor cells, mature fibroblasts, tenocytes or other cells to the device of the invention by adhering, incorporating, embedding or seeding the cells into the collagenous scaffold attached to the support matrix or to the support matrix directly. The exogenously added cells may induce production or produce proteins and matrix components consistent with neo-ligaments or neo-tendons or induce migration of the native cells from the uninjured ligament or tendons to the site of injury.

The cultured cells are advantageously added to the device of the invention, to the protective sleeve, to the support matrix as such or are adhered to a collagenous surface of the support matrix or scaffold before, during or even after the surgery, as already described above.

III. Biodegradable Tissue Adhesives

The method for repair and reconstruction of the injured or torn ligament and tendon is based on use of the biocompatible and biodegradable tissue adhesives. The tissue adhesives suitable for purposes of this invention must have certain properties to be suitable for the purposes of this invention.

The tissue adhesive must be biologically acceptable, compatible and easy to use. It must have relatively fast setting time and must possess required adhesive and cohesive properties. It also must be non-toxic, non-swelling and non-rigid to avoid causing abrasions or extrusion of the protective sleeve from the treatment site. Additionally, it must not interfere with the healing process or formation of new ligament or tendon tissue, or promote the formation of other interfering or undesirable tissues. It must also be bioresorbable and biodegradable by any acceptable metabolic pathway.

The adhesive must rapidly set within 0.5 to 10 minutes, preferably within 0.5-5 minutes, most preferably between 0.5 to about 3 minutes. However, the adhesive must not gel or polymerize too rapidly as it could cause problems during the surgery. Setting time shorter than 30 seconds is undesirable. Longer times than 10 minutes are not compatible with surgical time constraints. Additionally, the overall mode of use should be relatively simple because complex and lengthy procedures will not be accepted by surgeons.

Adhesive bonding is required to attach the adhesive to the frayed edges of the torn ligament and to glue, seal and support it. Minimal possessing peel strengths of the should be at least 3 N/m and preferably 10 to 30 N/m. Additionally, the adhesive must itself be sufficiently strong so that it does not break or tear internally, i.e., it must possess sufficient cohesive strength, measured as tensile strength in the range of 0.2 MPa, but preferably 0.8 to 1.0 MPa. Alternatively, a lap shear measurement which define the bond strength of the formulation should have values of at least 0.5 N/cm$^2$ and preferably 1 to 6 N/cm$^2$.

Typically, tissue adhesives suitable for purposes of this invention possessing the required characteristics are polymers. In the un-cured, or liquid state, such materials consist of freely flowable polymer chains which are not cross-linked together, but are neat liquids or are dissolved in physiologically compatible aqueous buffers. The polymeric chains also possess side chains or available groups which can, upon the appropriate triggering step, react with each other to couple or cross-link the polymer chains together. If the polymer chains are branched, i.e., comprising three or more arms on at least one partner, the coupling reaction leads to the formation of a network which is infinite in molecular weight, such as for example, a gel.

The formed gel has cohesive strength dependent on the number of inter-chain linkages, the length expressed as molecular weight of the chains between links, the degree of inclusion of solvent in the gel, the presence of reinforcing agents, and other factors. Typically, networks in which the molecular weight of chain segments between junction points (cross-link bonds) is between 100-500 Daltons are tough, strong, and do not swell appreciably. Networks in which the chain segments are between 500-2500 Daltons swell dramatically in aqueous solvents and become mechanically weak. In some cases the latter gels can be strengthened by specific reinforcer molecules; for example, the methylated collagen reinforces the gels formed from 4-armed PEGs of 10,000 Daltons (2500 Daltons per chain segment).

The gel's adhesive strength permits bonding to adjacent biological tissue by one or more mechanisms, including electrostatic, hydrophobic, or covalent bonding. Adhesion can also occur through mechanical inter-lock, in which the uncured liquid flows into tissue irregularities and fissures, then, upon solidification, the gel is mechanically attached to the tissue surface.

At the time of use, usually some type of triggering action is applied. For example, it can be the mixing of two reactive partners, it can be the addition of a reagent or buffer to raise the pH, or it can be the application of heat or light energy.

Once the adhesive is in place, it must be non-toxic to adjacent tissue, and it must be incorporated into the tissue and retained permanently, degraded in situ, or be naturally removed, usually by hydrolytic or enzymatic degradation. Degradation can occur internally in the polymer chains, or by degradation of chain linkages, followed by diffusion and removal of polymer fragments dissolved in physiological fluids.

Another characteristic of the tissue adhesive is the degree of swelling it undergoes in the tissue environment. Excessive swelling is undesirable, both because it creates pressure and stress locally, and because a swollen gel losses tensile strength, due to the plasticizing effect of the imbibed solvent which, in this case, is physiological fluid. Gel swelling is modulated by the hydrophobicity of the polymer chains. In some cases it may be desirable to derivatize the base polymer of the adhesive so that it is less hydrophilic. For example, one function of methylated collagen within the adhesive is presumably to control swelling of the gel. In another example, the adhesive made from penta-erythritol tetra-thiol and polyethylene glycol diacrylate can be modified to include polypropylene glycol diacrylate, which is less hydrophilic than polyethylene glycol. In a third example, adhesives containing gelatin and starch can be methylated both on the gelatin and on the starch, again to decrease hydrophilicity.

The biodegradable tissue adhesive is typically a polymer having a rapid polymerization time with a sufficiently fast setting time to set the tissue adhesive within about a half to about ten minutes, preferably one to three minutes, most preferably within one minute, and a sufficient strength to hold two edges of a ruptured ligament or tendon together when such ligament or tendon is subjected to stretching.

Tissue adhesive of the invention is a biologically acceptable typically rapidly gelling formulation having a specified range of adhesive and cohesive properties and is thus a biologically acceptable rapidly gelling synthetic compound having adhesive and/or gluing properties. The tissue adhesive is typically a hydrogel, such as derivatized polyethylene glycol (PEG), or a protein, such as albumin, which is preferably cross-linked with a collagen compound. The tissue adhesive of the invention typically gels and/or bonds rapidly upon contact with tissue, particularly with tissue containing collagen.

Preferred tissue adhesives are the adhesive hydrogels. The adhesive hydrogel is a biologically acceptable rapidly gelling synthetic compound having adhesive and/or gluing properties, such as derivatized polyethylene glycol (PEG) which is cross-linked with a collagen compound, typically alkylated collagen. Examples of suitable hydrogels are tetra-hydroxysuccinimidyl or tetra-thiol derivatized PEG, or a combination thereof, commercially available from Cohesion Technologies, Palo Alto, Calif. under the trade name CoSeal™, described in *J. Biomed. Mater. Res Appl. Biomater.*, 58:545-555 (2001), or two-part polymer compositions that rapidly form a matrix where at least one of the compounds is polymeric, such as, polyamino acid, polysaccharide, polyalkylene oxide or polyethylene glycol and two parts are linked through a covalent bond, as described in U.S. Pat. No. 6,312,725B1, herein incorporated by reference, and cross-linked PEG with methylated collagen, such as a cross-linked polyethylene glycol hydrogel with methylated collagen. The synthetic compound may be also PEG or derivatized polyethylene glycol and may also contain, for example, a protein, such as, for example, albumin. The adhesive of the invention gels and/or bonds rapidly and strongly upon contact with ligament or tendon tissue.

Tissue adhesive for gluing together the two pieces of the torn ligament or tendon are additionally selected from a highly adhesive hydrogel complexes comprising, for example, a mixture of at least collagen or derivatized collagen and polyethylene glycol or derivatized polyethylene glycol. Other components, such as fibroblasts, tenocytes, mesenchymal or embryonic cells, synovial tissue, blood cloth or healing accelerators may be added to the complex.

Additionally, structural hydrogel in form of the support matrix, for example collagen honeycomb, collagen sponge or collagen scaffold may be used in conjunction with the highly adhesive hydrogels.

The most preferred tissue adhesive is methylated collagen-PEG hydrogel. This hydrogel strongly binds the torn region during the period of healing and also permits or induces cell migration and extracellular matrix formation in the torn zone.

With respect to long-term binding, collagen-PEG hydrogel complex, particularly where the collagen is methylated collagen, has much stronger adhesive properties than PEG alone, collagen alone, or fibrin-based adhesives, and it is far more biocompatible than epoxies or gluteraldehyde cross-linked materials and the like. Additionally, since these collagen-PEG hydrogels are biologically acceptable and biodegradable, they biodegrade slowly and can thus remain at the site of injury for weeks or months without any detrimental consequences.

With respect to the ligament or tendon healing, collagen-PEG hydrogels contain a network of Type I collagen which provides suitable environment for cell migration from the torn pieces of the ligament. Additionally, PEG is also a friendly substrate for cell migration.

Another acceptable adhesive is made from a copolymer of polyethylene glycol and polylactide, polyglycolide, polyhydroxybutyrates or polymers of aromatic organic amino acids and sometimes further containing acrylate side chains, gelled by light, in the presence of some activating molecules.

The invention is intended to include the use of all tissue adhesives having strong adhesive properties.

I. Method for Repair and Reconstruction of Ruptured Ligament and Tendons

The method of the invention for repair and reconstruction of the injured or ruptured ligaments or tendons according to the invention comprises several steps including selecting appropriate materials for fabrication of a protective sleeve, selecting an appropriate material to be used as a supporting matrix and a tissue adhesive to hold the frayed edges of a torn ligament together, surgically attaching the protective sleeve to the uninjured portions of ligaments or tendons, to the bones or to the muscles, applying the tissue adhesive during the surgery, protecting the ligament or tendon treated with the adhesive from the tensile and rotational forces and strain and generally providing conditions for healing of the ligament into the healthy tissue. The same steps are involved in repair and reconstruction of the tendons, except that one side of the torn tendon is attached to the muscle.

The method for repair and reconstruction of ruptured ligaments or tendons and restoration of their function comprises the following steps:

(a) fabricating a protective sleeve that has flexibility and contractibility permitting its contraction and compression with extension of said sleeve;

(b) selecting a biologically acceptable biodegradable tissue adhesive having a sufficiently fast setting time to set the tissue adhesive within several minutes to have a sufficient strength to hold two or more frayed edges of ruptured ligaments or tendons together for at least a time needed for healing of said rupture or injury, and that permits such ruptured ligaments or tendons to withstand the stress when subjected to stretching or other normal physiological activity during the healing period and that biodegrade thereafter;

(c) surgically attaching one end of the protective sleeve to the uninjured portion of ligament or tendon, or to the bone where the unruptured healthy ligament or tendon is attached.

(d) surgically stably juxtaposing the two or more frayed edges of the ruptured ligament or tendon to a close proximity of each other wherein said proximity largely corresponds to the unruptured healthy ligament or tendon;

(e) applying said tissue adhesive to said juxtaposed frayed edges of the torn ligament or tendon and sealing a space between these frayed edges of the ruptured ligament or tendon with said tissue adhesive;

(f) pulling over or otherwise covering the juxtaposed frayed edges of the ruptured ligaments or tendons sealed with the tissue adhesive with the protective sleeve;

(g) attaching a second end of the protective sleeve to the uninjured portion of the ligament or tendon or to the bone where the other end of the unruptured ligament is normally attached or to the muscle where the unruptured tendon is normally attached; and (h) stabilizing a site of the injury by limiting weight bearing and/or range of motion for a time needed for the frayed edges of the ruptured ligament or tendon to grow together and for the rupture to heal;

wherein said protective sleeve for repair and reconstruction of the ruptured ligaments or tendons comprises a biodegradable fibrous sheet, mesh, netting or matrix wherein said protective sleeve is combined with a support made of the biodegradable material that is flexible, contractible and strong enough to withstand a tension largely corresponding to the tension to which the healthy functioning ligament or tendon is exposed and that is suitable for temporary attachment to the bone where the healthy ligament is attached or to the muscle where the healthy tendon is attached.

The protective sleeve, the support matrix and the tissue adhesive must be selected, prepared, obtained or fabricated before the surgery.

The protective sleeve that has flexibility and contractibility permitting its contraction with extension of the sleeve over, and compression of, the frayed edges of the ruptured ligament or tendon treated with the tissue adhesive. The protective sleeve is selected and its size is determined based on the type and extent of the injury and on the site of attachment. The size of the protective sleeve may be from the whole length of the healthy uninjured ligament or tendon to the small 1-3 cm long protective sleeve. Typically, the protective sleeve is prefabricated and prepackaged together with the support matrix in sterile ready to use form.

The tissue adhesive is preferably the PEG cross-linked with the methylated collagen. The adhesive is supplied for in for use packaging and is applied to the site of injury in liquid or semi-liquid form.

If exogenous cells are to be added to the support matrix, these cells are provided in a sterile form and in sufficient number for seeding within the support matrix and are typically added just before the surgery and may be added even after the protective sleeve is in place.

At the beginning of the surgery, after the surgeon determines the extent of the injury and cleans up the wound, the surgeon selects the site of attachment and based on the site of the attachment and on the extent of the injury or tear selects the length and size of the protective sleeve and attaches the sleeve either to the uninjured portion of the ligament or tendon or to the bone or muscle, on one side only using surgical stitches, staples or other means of attachment.

Surgeon then stably juxtapositions the frayed edges of the ruptured ligament or tendon to a close proximity of each other taking care to, as much as possible, achieve a proximity largely corresponding to the uninjured healthy ligament or tendon and immediately applies the tissue adhesive to the juxtaposed frayed edges of the torn ligament or tendon. The said tissue adhesive holds the juxtaposed frayed edges of the torn ligament or tendon together and seals a space between the frayed edges.

The surgeon then pulls over or otherwise covers the sealed tear of the ruptured ligaments or tendons with the protective sleeve and attaches the second end of the protective sleeve to the uninjured ligament or tendon or to the bone or muscle, as appropriate.

After finishing the surgery, the site is stabilized at least for a certain time to allow for healing of the wound to proceed.

The method and several of its steps are illustrated in representations seen in FIGS. 4-8.

Figure 4A:
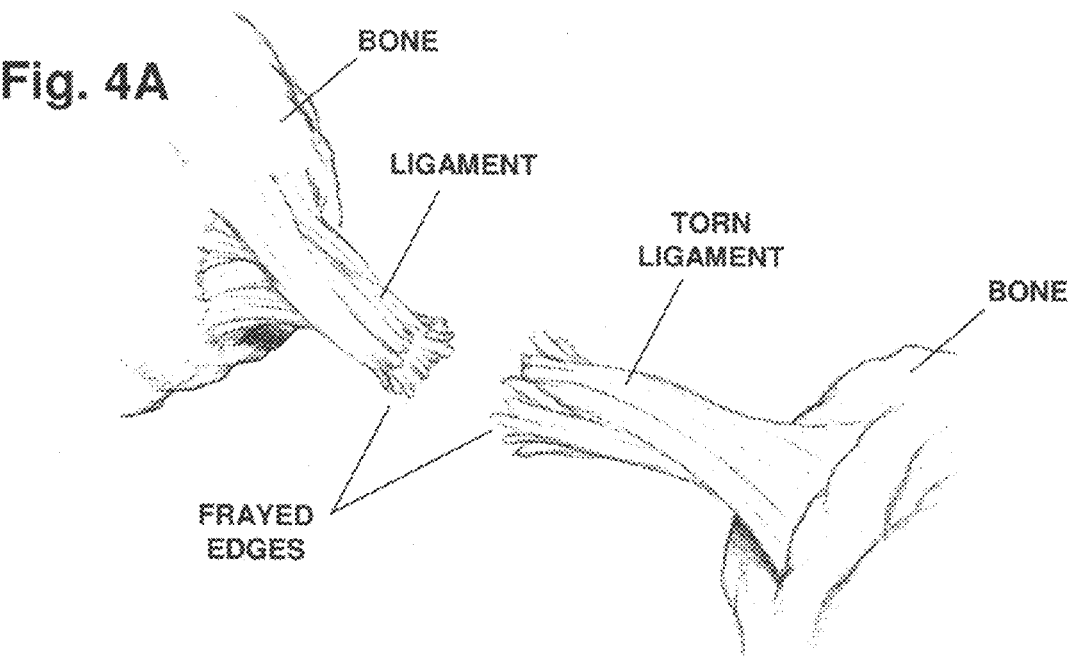
FIG. 4A is a schematic representation of a ruptured ligament showing a tear, two portions of the torn ligament, frayed edges of the torn ligament and attachment of the ligament to the bone on each side.

FIG. 4A is a schematic representation of a ruptured ligament showing a ligament torn into two parts. Two edges of the torn ligament are seen as being pulled from each other by the tensile strain asserted by the two bones where the torn pieces of ligament are attached. Each torn piece of the ligament remains attached to the bone.

Figure 4B:
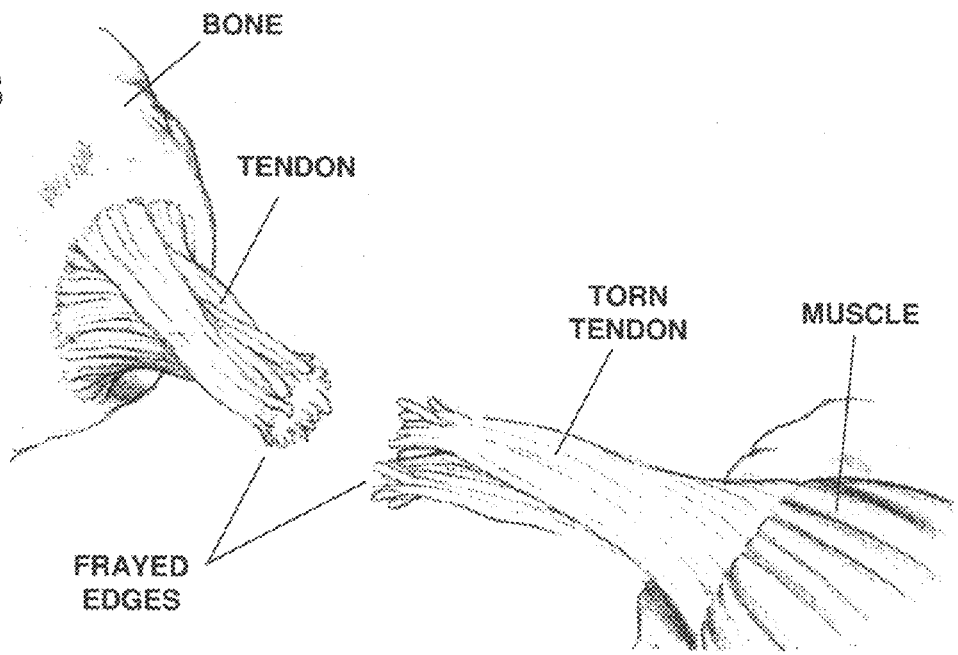
FIG. 4B is a schematic representation of a ruptured tendon showing a tear, two portions of the torn tendon, frayed edges of the torn tendon and attachment of the tendon to the bone on one side and to the muscle on the other side.

FIG. 4B is a schematic representation of a ruptured tendon showing a tear, two edges of the torn tendon and attachment of the tendon to the bone on one side and to the muscle on the other side.

As seen in FIGS. 4A and 4B, the torn ligament or tendon are, following the injury, separated into two pieces with each piece having frayed edges at a site of tear with other end remaining attached either to the bone (ligament) or to the bone and muscle (tendon). In order to successfully treat the injury, frayed edges of the torn ligament or tendon must be brought together under conditions that will permit the ligament or tendon growing back together without being constantly pulled from each other by the strain exerted by the surrounding tissue. Without a protective shield placed around the torn ligament or tendon treated with the adhesive, the healing of the ligament or tendon cannot be accomplished. The process may be advantageously augmented by addition of the mature and pre-cultured tenocytes or fibroblasts or immature progenitor cells, as discussed above.

FIG. 5A illustrates a step of applying an adhesive compound to the site of the tear and to the immediate vicinity of the tear. As seen from the FIG. 5A, the adhesive is applied on top of, in between and around the torn frayed edges of the two pieces of the torn ligament and also covers the immediate vicinity of the tear of the ruptured ligament so that not only the tear is glued together but the adhesive also covers a certain portion of the uninjured ligament close to the tear. In this arrangement, the adhesive assists in holding the frayed edges and pieces of the torn ligament together for a time need for complete healing. The adhesive compound is typically a collagen containing polymer or a copolymer that is applied as a solution which gels or solidifies upon contact with the tissue or due to changes in temperature, as already discussed in greater detail. FIG. 5B similarly illustrate the same step for repair and reconstruction of the ruptured tendon.

Figure 6A:
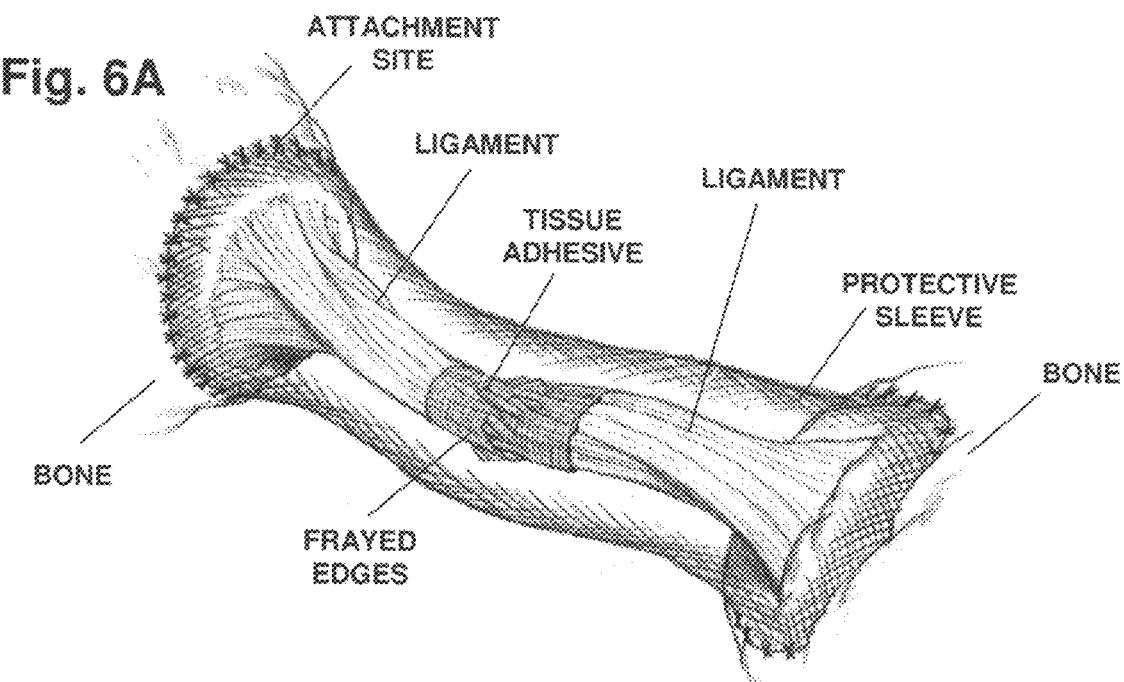
FIG. 6A is a schematic representation of a ruptured ligament where the frayed edges of the torn ligament are treated with a tissue adhesive and wherein the ruptured and treated ligament is further encased in a flexible and contractible protective sleeve that is able to contract upon extension of said sleeve and compress an area treated with the tissue adhesive where the protective sleeve is shown to be surgically attached to the bone on each side of the ruptured ligament.
Figure 6B:
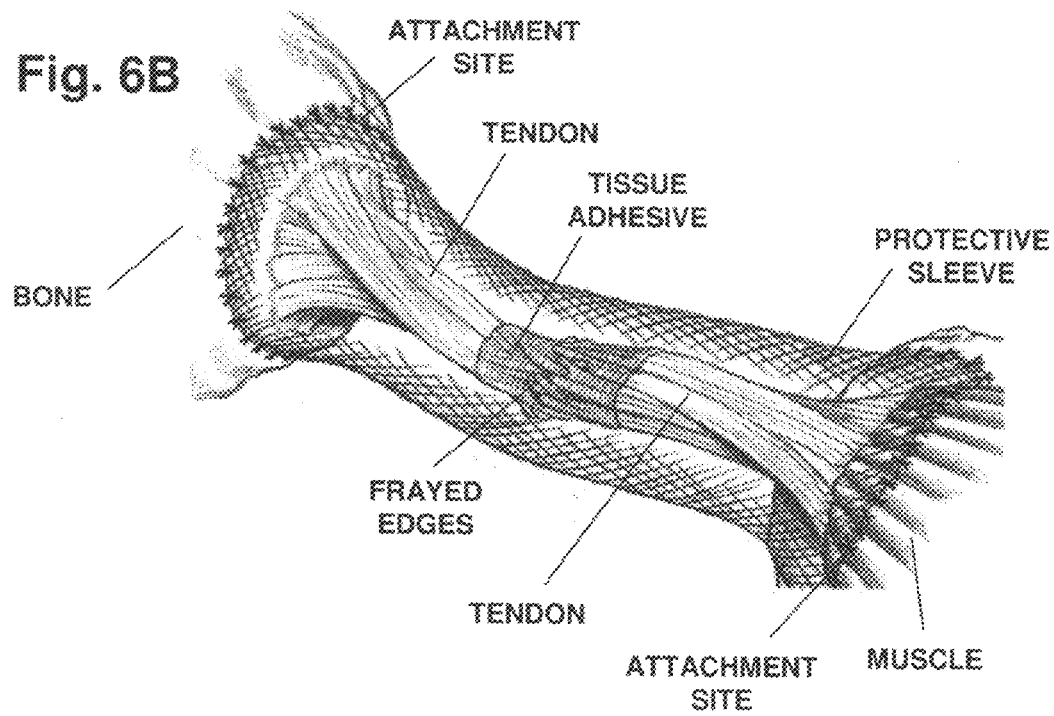
FIG. 6B is a schematic representation of a ruptured tendon where the frayed edges of the torn tendon are treated with a tissue adhesive and wherein the ruptured and treated tendon is further encased in a flexible and contractible protective sleeve that is able to contract upon extension of said sleeve and compress an area treated with the tissue adhesive where the protective sleeve is shown to be surgically attached to the bone on one side and to the muscle on the other side of the torn tendon.

A process for repair and reconstruction of ruptured ligament or tendon then continues as illustrated in FIGS. 6A and 6B. FIG. 6A is a schematic representation of a ruptured ligament treated with an adhesive, as seen in FIG. 5A, wherein the ruptured and treated ligament is further encased in a protective sleeve surgically attached, in this figure, to the bone on each side of the ruptured ligament. The protective sleeve is shown in FIG. 8A in its pre-operative state and rolled into the sleeve to be emplaced around the treated ruptured ligament (FIG. 8B). The protective sleeve may also be attached to the uninjured portions of the ligament.

The protective sleeve forms a protective shield acting as an encasement for a ruptured ligament treated with a tissue adhesive under conditions promoting healing. The sleeve is a sheet of fibrous material, mesh, net or a composite of the protective sleeve with a support matrix (FIG. 8A) rolled around the ruptured and treated ligament (FIG. 8D) and attached to the bone on either side (FIGS. 8A-8D). In a preferred alternative, the sleeve is a rolled up tube of the fibrous sheet, mesh, net or the sleeve/matrix composite that is first pulled over one part of the torn ligament and attached to the bone or uninjured ligament on that side, then the frayed edges of the torn ligament are pulled together and the adhesive is applied to the tear and into the space in the near vicinity of the tear to hold and glue the two frayed edges together. Before or after the adhesive is fully polymerized, the protective sleeve or composite is pulled over the treated ligament and attached to the bone on the other side. In alternative, before or after the torn ligament is glued together and the adhesive is fully polymerized, the additional tissue adhesive, still in the liquid form, is added to fill the protective sleeve and is allowed to polymerize to further strengthen the glued together ruptured edges of the ligament or tendon.

In this form, the protective sleeve acts as a protective shield for the ruptured ligament treated with the adhesive glue against tensions to which the ligament or tendon is subjected during a normal physical activity which tension, if not controlled by the protective sleeve or shield, would cause the two pieces of the ruptured ligament to separate and prevent healing of the ligament. Because of its material, which is preferably stretchable but firm, the ligament or tendon treated with the tissue adhesive is not subjected to any strain from the bones to which the ligament is naturally attached.

FIG. 6B is a schematic representation of a ruptured tendon treated with an adhesive wherein the ruptured and treated tendon is further encased in a protective sleeve surgically sewn to the bone on one side and to the muscle on the other side of the torn tendon.

Figure 7A:
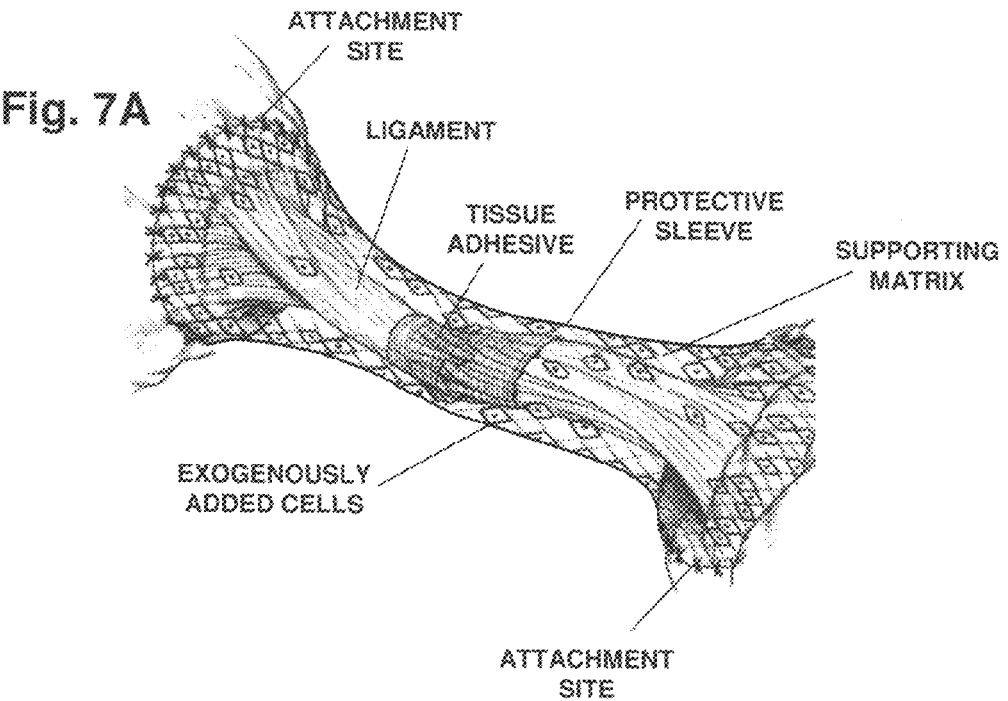
FIG. 7A is a schematic representation of a ruptured ligament seen in FIG. 6A, treated with an adhesive wherein the ruptured and treated ligament is further encased in a protective sleeve surgically attached to the bone on each side of the ruptured ligament wherein said sleeve is a composite of the protective sleeve with a support matrix embedded with exogenously added cells and may optionally also contain growth factors, modulators or other agents (not shown).

In order to achieve rapid and complete healing, additional compounds, particularly those promoting the growth and healing of connective tissue may be added either to the adhesive glue or to the material used for formation of the protective sleeve or supporting matrix. FIG. 7A illustrates an arrangement where the cells, such as fibroblasts or tenocytes, or in alternative, their respective progenitors, are added to the material used as a protective sleeve. Other compounds, such as growth hormones, modulators of the growth or pharmaceutical agents may also be advantageously added to the adhesives or to the sleeve or matrix materials.

Figure 7B:
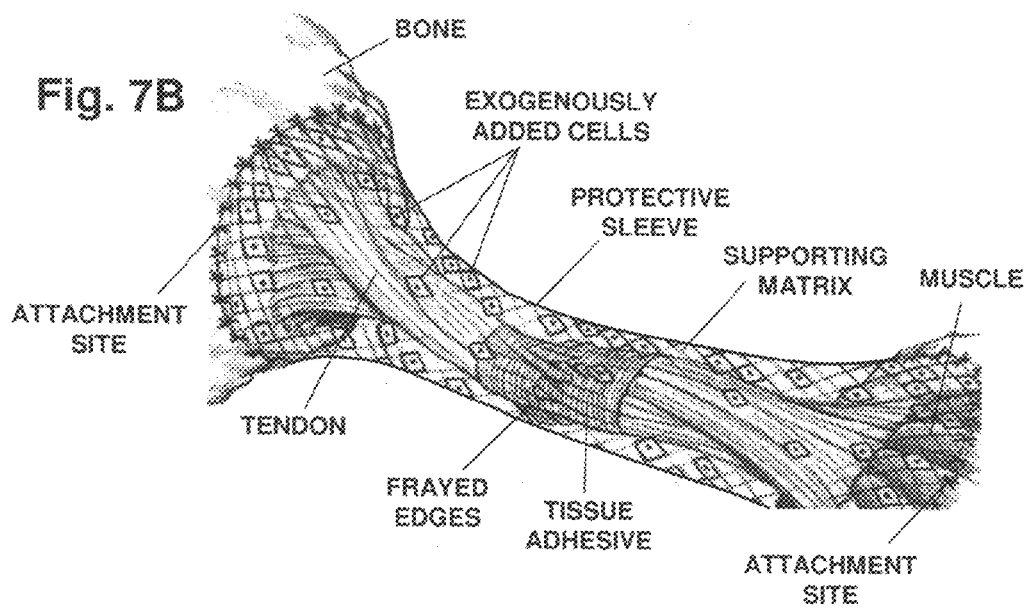
FIG. 7B is a schematic representation of a ruptured tendon seen in FIG. 6B, treated with an adhesive wherein the ruptured and treated tendon is further encased in a protective sleeve surgically attached to the bone on one side and to the muscle on the other side of the torn tendon wherein said sleeve is a composite of the protective sleeve with a support matrix embedded with exogenously added cells and may optionally also contain growth factors, modulators or other agents (not shown).

FIG. 7A is a schematic representation of a ruptured ligament treated with an adhesive wherein the ruptured and treated ligament is further encased in a protective sleeve surgically attached to the bone on each side of the ruptured ligament wherein said sleeve is fabricated from a matrix-like material having embedded within fibroblasts, tenocytes or their progenitor cells. FIG. 7B is a corresponding process for treatment of the tendon.

FIG. 8A, already discussed above, is a schematic representation of a protective sleeve before being used for encasement of a torn ligament or tendon. Before being rolled into a sleeve, the material is supplied typically as a sheet of material having optionally embedded into it fibroblasts, tenocytes, a mixture of both, alone, or in a combination with hormones, such as a growth hormones or modulators, or pharmaceutical agents that would promote healing and prevent infection. The sheet of material used as a protective sleeve has two ends which are surgically attached either to the bones or to the bone and muscle, depending if such material is used for protecting the ligament or tendon rupture. FIG. 8B shows the sheet of material rolled into the protective sleeve for use also showing the two ends that are attached, typically with surgical stitches, to the bone or muscle. FIG. 8C shows the protective sleeve seen in FIG. 8B in use for covering and protecting the torn and treated ligament according to the invention where the flexible and contracting material is seen in its extended form clearly showing a compression site. FIG. 8D shows the compression of the frayed edges glued together encased within the constrains of the protective sleeve.

Individual steps of the method for repair and reconstruction of ruptured ligaments and tendons are listed below and each step is described in greater details.

A process of gluing the edges of the ruptured ligament with a tissue adhesive and surrounding or enveloping it with a protective sleeve that has a length corresponding to the length of the normal healthy uninjured ligament or tendon is combined with a surgical attachment of the sleeve to the bone. The encasement permits the ligament to heal within confines of the physiological tension parameters existing under normal conditions.

Surgical attachment of the protective sleeve may be performed in two ways, depending on which shape of the protective sleeve is used. In case that the protective sleeve is supplied as a rectangular sheath (FIG. 8A), the two edges of the sheet are at least partially attached to the two bones or uninjured portion of the ligament, the adhesion of the two ruptured edges of the ligament is performed and the sheath is rolled into a tube (FIG. 8B) surrounding the treated ligament. The rest of the sheath is attached to the bone or uninjured ligament to hold the sleeve in place.

In alternative, even more simple method of constructing the protective sleeve is to provide a knitted flat rectangle sheath and roll this sheath around the two edges of torn ligament glued together with the tissue adhesive and suture or glue this roll-up tube to the bone.

In case that the protective sleeve is supplied already as a tube (FIG. 8B), one end of the protective sleeve is attached to the bone where the healthy unruptured ligament or tendon is attached by way of slipping the sheath down over the longer of the two frayed edges of the torn ligament, performing the adhesion of the two edges of the torn ligament and then slipping it over the treated site before or after applying the tissue adhesive. This embodiment requires fabricating the sleeve as an open-ended tube.

UTILITY

The current invention provides a practical method for treatment of ruptured ligaments and tendons. The method of the invention provides conditions for maintaining of the ruptured ligament or tendon in an immobilized state for a period of time needed for ligament or tendon healing and provide other conditions enabling and promoting such healing.

The method for treatment of the ruptured ligament or tendon comprises steps of surgically positioning the two edges of the ruptured ligament or tendon to a close proximity of each other wherein said proximity corresponds to the unruptured healthy ligament or tendon, gluing the two edges together using a biologically acceptable biodegradable tissue adhesive as well as sealing a space between and around the two edges of the ruptured ligament or tendon with the same adhesive, covering a sealed space with the protective sleeve by slipping one end of the protective sleeve over one of the ruptured edges and attaching a first end of the protective sleeve to the bone where the ligament is attached, extending the protective sleeve over the glued together region and attaching the second end of the protective sleeve to the bone where the other end of the ligament is attached or to the muscle where the tendon is attached, optionally filling the space between the glued together edges and the protective sleeve with a supporting matrix, typically made of a different material than the material used for protective sleeve. The support matrix may, as discussed above contain a progenitor or mature fibroblasts or tenocytes and may also contain the growth promoting factors and agents as well as other agents, such as for example, pharmaceutical agents inhibiting development of infections or promoting healing, among others. The treated joint is then immobilized for a certain time needed for the two edges of the ruptured ligament to grow together and the rupture is heal.

What is claimed is:

1. A method for in situ repair and reconstruction of injured ligaments and tendons comprising steps of:
    (a) fabricating a protective sleeve or a composite of the protective sleeve with a support matrix wherein said sleeve or said composite has flexibility and contractibility permitting its contraction and compression with extension of said sleeve;
    (b) selecting a biologically acceptable biodegradable tissue adhesive having a setting time of adhesion in from about 30 seconds to about five minutes, peel strengths of at least 3N/m, tensile strength in the range of 0.8 to 1.0 MPa, and a bond strength from 1 to 6 $N/cm^2$, to have a sufficient strength to hold frayed edges of a ruptured ligament or tendon together for a time needed for said frayed edges of said ligament or tendon to grow together;
    (c) surgically attaching, in situ, one end of the protective sleeve or said composite to the uninjured portion of ligament or tendon, or to the bone where the uninjured healthy ligament or tendon is attached;
    (d) immobilizing, in situ, said injured ligament or tendon by surgically juxtaposing the frayed edges of the ruptured ligament or tendon to a close proximity of each other and connecting said frayed edges together using said biologically acceptable biodegradable tissue adhesive and sealing a space between and around the two edges of the ruptured ligament or tendon with said adhesive;
    (e) applying, in situ, said tissue adhesive to a top of, around or in between said juxtaposed frayed edges of step (d) thereby attaching said frayed edges together and sealing an area around and between said edges with said adhesive;
    (f) extending, in situ, said protective sleeve or said composite over and covering a sealed area of step (e) with said protective sleeve or said composite;
    (g) attaching, in situ, a second end of said protective sleeve or said composite o an uninjured portion of the ligament or tendon or to a bone where the other end of the uninjured ligament is attached, or to a muscle where the uninjured tendon is attached; and
    (h) stabilizing a site of the injury by limiting weight bearing and/or range of motion for a time needed for the frayed edges of the ruptured ligament or tendon to grow together.

2. The method of claim 1 wherein said protective sleeve or said composite is fabricated as a sheet, mesh, strands, fibers, net, fibrous sheet, fibrous mesh, fibrous netting, or from a knitted sheath comprising individual strands of yarn.

3. The method of claim 2 wherein said protective sleeve or said composite is fabricated from a biodegradable silk, a porous collagen matrix, a derivatized polymer, a bundle of yarn strands comprising one to several fibers of polymer or silk.

4. The method of claim 2 wherein a material used for fabrication of said protective sleeve or said composite is selected from the group consisting of Type I collagen, Type II collagen, Type IV collagen, gelatin, agarose, collagen containing proteoglycan, glycosaminoglycan or glycoprotein, polymer of aromatic organic acid, fibronectin, laminin, bioactive peptide growth factor, cytokine, elastin, fibrin, synthetic polymeric fibers made of polylactic, polyglycolic or polyamino acid, polycaprolactone, polyamino acid, polypeptide gel, copolymer thereof and a combination thereof.

5. The method of claim 2 wherein a material used for fabrication of a support matrix of said composite is a sol, gel, sol-gel or themio-reversible hydrogel.

6. The method of claim 1 wherein said supporting matrix of said composite is incorporated with, have embedded into or is seeded with exogenously added cells.

7. The method of claim 6 wherein said cells are fibroblasts, tenocytes, their progenitor cells, mesenchymal cells, embryonic cells or stem cells.

8. The method of claim 7 wherein said cells are adhered to a surface of said support or into said protective sleeve.

9. The method of claim 7 additionally comprising growth hormones, modulators of cell growth or pharmaceutical agents.

10. The method of claim 7 wherein said cells are autologous fibroblasts or autologous tenocytes.

11. The method of claim 1 wherein said tissue adhesive is a biologically acceptable polymer having a polymerization setting time between about one and about three minutes.

12. The method of claim 11 wherein said tissue adhesive is selected from the group consisting of a derivatized polyethylene glycol (PEG); albumin cross-linked with a collagen compound; polyethylene glycol (PEG) cross-linked with a collagen compound; tetra-hydrosuccinimidyl derivatized PEG; tetra-thiol derivatized PEG;
    two-part polymer composition that rapidly foiin a matrix where at least one of the compounds is polyamino acid, polysaccharide, or polyalkylene oxide; polyethylene glycol;
    polyethylene glycol cross-linked with methylated collagen; a copolymer of polyethylene glycol and polylactide; a copolymer of polyethylene glycol and polyglycolide, a copolymer of polyethylene glycol and polyhydroxybutyrate; a polymer of an aromatic organic amino acid; a copolymer thereof, and a combination thereof.

13. The method of claim 12 wherein the tissue adhesive material is polyethylene glycol cross-linked with methylated collagen.

14. The method of claim 12 wherein said adhesive is polyhydroxybutyrate.

15. A device for in situ repair and reconstruction of injured ligament or tendon comprising a protective shield acting as an encasement for said injured ligament or tendon wherein said protective shield comprises
    a flexible, contractible and biodegradable composite comprising a protective sleeve and a collagenous support matrix, said protective shield configured to be positioned, in situ, around and surrounding an injured ligament or tendon treated with a methylated collagen polyethylene glycol tissue adhesive;
    wherein said support matrix of said composite is positioned, in situ, adjacent to said injured ligament or tendon and is further incorporated with, have embedded into or is seeded with exogenously added fibroblasts, tenocytes, fibroblast progenitors, tenocyte progenitors, mesenchymal cells, embryonic cells or stem cells;

wherein said support matrix is a porous sponge, honeycomb, lattice or scaffold fabricated from Type I collagen, Type II collagen, Type IV collagen derivatized collagen, cross-linked collagen, collagen containing proteoglycan, collagen containing glycosaminoglycan or collagen containing glycoprotein, a mixture thereof or a combination thereof;

wherein said protective sleeve is fabricated from a fibrous material comprised of a group of fibers having different times of degradation, wherein at least some fibers are predetermined to have degradation time from about three to about six months; and wherein said protective sleeve is a fibrous sheath, fibrous mesh, fibrous net, fibrous strand, fibrous yarn, fibrous strand or knitted fiber wherein said fibers having the different time of degradation provide a gradual degradation of the protective sleeve and wherein during said gradual degradation of said protective sleeve the injured ligament or tendon is gradually subjected to decreasing tensile strength;

wherein a first group of fibers to degrade supports a deposition and a growth of an incipient ligament-producing fibroblast positioned adjacent to the injured ligament or a growth of an incipient tendon-producing tenocyte positioned adjacent to the injured tendon, wherein a degradation time for the first fiber is about or less than one month and wherein the first fiber is a derivatized block polyethylene glycol (PEG);

wherein a second group of fibers to degrade reinforces a strength of the protective sleeve and wherein a degradation time for the second group of fibers is from about one to about two months and wherein said second fiber is a microbially synthesized polyester polyalkanoate; and wherein a third group of fibers to degrade provides a long-term backbone support for the protective shield and wherein a degradation time of the third group of fibers is from about three to about six months;

wherein said flexible and contractible composite is extendable and, when extended. it compresses frayed edges of an injured ligament or tendon juxtaposed together and covered with said tissue adhesive and holds said frayed edges together; and wherein said composite comprises attachment means for attaching, in situ, a first end of said protective shield to a bone where a ligament is attached, or to a muscle where a tendon is attached, a means for protecting said frayed edges of an injured ligament or tendon juxtaposed together and covered with said tissue adhesive by extending said protective shield over said frayed edges, and a means for attaching a second end of said protective sleeve to an apposite bone or muscle where the other end of the ligament is attached.

16. The device of claim 15 wherein said cells are added to said support matrix or are adhered to a collagenous surface of said support matrix before, during or after a surgery.

* * * * *